(12) United States Patent
Tilson et al.

(10) Patent No.: US 10,278,682 B2
(45) Date of Patent: May 7, 2019

(54) SHEATHS FOR MEDICAL DEVICES

(75) Inventors: Alexander Quillin Tilson, Burlingame, CA (US); Mark Christopher Scheeff, San Francisco, CA (US); Roland J. Downs, Mesa, AZ (US); Christopher Michael Adams, Tempe, AZ (US); Jon Michael Holweger, Queen Creek, AZ (US)

(73) Assignee: LOMA VISTA MEDICAL, INC., Tempe, AZ (US)

( * ) Notice: Subject to any disclaimer, the term of this patent is extended or adjusted under 35 U.S.C. 154(b) by 902 days.

(21) Appl. No.: 12/537,166

(22) Filed: Aug. 6, 2009

(65) Prior Publication Data

US 2011/0087070 A1 Apr. 14, 2011

Related U.S. Application Data

(63) Continuation-in-part of application No. 12/512,878, filed on Jul. 30, 2009, now abandoned, which is a
(Continued)

(51) Int. Cl.
| | |
|---|---|
| *A61B 17/00* | (2006.01) |
| *A61B 90/11* | (2016.01) |
| *A61B 34/30* | (2016.01) |
| *A61B 90/00* | (2016.01) |
| *A61B 34/20* | (2016.01) |

(Continued)

(52) U.S. Cl.
CPC ...... *A61B 17/00234* (2013.01); *A61B 1/0055* (2013.01); *A61B 1/00135* (2013.01); *A61B 1/07* (2013.01); *A61B 1/31* (2013.01); *A61B 5/4836* (2013.01); *A61B 5/6847* (2013.01); *A61B 34/20* (2016.02); *A61B 34/30* (2016.02); *A61B 90/11* (2016.02); *A61B 90/39* (2016.02)

(58) Field of Classification Search
CPC ...... A61M 25/00; A61M 5/178; A61M 37/00; A61M 1/008; A61M 25/0017; A61F 2/00; A61F 2/915; A61B 5/00; A61B 6/00; A61B 8/14; A61B 1/00; A61B 17/12022; A61B 17/22; A61B 1/0011; F16L 33/225
USPC .... 606/1; 604/526, 527, 103.09, 524, 93.01, 604/96.01; 600/585, 463, 434, 101; 623/1.11; 128/207.15
See application file for complete search history.

(56) References Cited

U.S. PATENT DOCUMENTS 4,705,511 A * 11/1987 Kocak ........................... 604/524
4,737,153 A * 4/1988 Shimamura et al. ......... 604/526
(Continued)

OTHER PUBLICATIONS

Ultimate tensile strength From Wikipedia, the free encyclopedia This page was last modified on Feb. 21, 2015, Text is available under the Creative Commons Attribution-ShareAlike License.*

*Primary Examiner* — Carl H Layno
*Assistant Examiner* — Qingjun Kong
(74) *Attorney, Agent, or Firm* — King & Schickli, PLLC

(57) ABSTRACT

A device is disclosed for therapeutic and/or diagnostic use in or on a patient's body. The device can have a sheath and a tool. The sheath can be made, at least in part, from a laminate. The laminate can have reinforcement fibers in longitudinal, latitudinal, helical, and/or other configurations around the sheath. The tool can be at least partially within the sheath. The tool can be attached to the sheath at one or more lengths along the tool. The sheath can be removed from the tool and replaced.

16 Claims, 36 Drawing Sheets

Related U.S. Application Data continuation of application No. PCT/US2008/052535, filed on Jan. 30, 2008, application No. 12/537,166, which is a continuation-in-part of application No. 12/512,809, filed on Jul. 30, 2009, now Pat. No. 10,188,273, which is a continuation of application No. PCT/US2008/052542, filed on Jan. 30, 2008, application No. 12/537,166, which is a continuation of application No. PCT/US2009/041637, filed on Apr. 29, 2009, and a continuation-in-part of application No. 12/477,005, filed on Jun. 2, 2009, now abandoned, and a continuation-in-part of application No. 12/477,048, filed on Jun. 2, 2009, now abandoned.

(60) Provisional application No. 60/887,319, filed on Jan. 30, 2007, provisional application No. 60/887,323, filed on Jan. 30, 2007, provisional application No. 60/949,219, filed on Jul. 11, 2007, provisional application No. 61/057,986, filed on Jun. 2, 2008, provisional application No. 61/086,739, filed on Aug. 6, 2008, provisional application No. 61/105,385, filed on Oct. 14, 2008, provisional application No. 61/205,866, filed on Jan. 22, 2009, provisional application No. 61/125,720, filed on Apr. 27, 2008.

(51) Int. Cl.

| | | |
|---|---|---|
| *A61B 1/07* | (2006.01) | |
| *A61B 5/00* | (2006.01) | |
| *A61B 1/005* | (2006.01) | |
| *A61B 1/31* | (2006.01) | |
| *A61B 1/00* | (2006.01) | |

(56) References Cited

U.S. PATENT DOCUMENTS

| | | | |
|---|---|---|---|
| 5,057,092 A * | 10/1991 | Webster, Jr. | 604/527 |
| 5,069,674 A * | 12/1991 | Fearnot | A61M 25/0045 604/523 |
| 5,178,158 A * | 1/1993 | de Toledo | 600/585 |
| 5,251,640 A * | 10/1993 | Osborne | 600/585 |
| 5,653,697 A * | 8/1997 | Quiachon et al. | 604/528 |
| 5,669,383 A * | 9/1997 | Johnson | A61B 5/06 324/219 |
| 5,702,373 A * | 12/1997 | Samson | 604/527 |
| 5,713,867 A * | 2/1998 | Morris | A61M 25/0668 604/164.05 |
| 5,728,063 A * | 3/1998 | Preissman et al. | 604/103.09 |
| 5,795,341 A * | 8/1998 | Samson | 604/526 |
| 5,891,114 A * | 4/1999 | Chien et al. | 604/527 |
| 5,997,487 A * | 12/1999 | Kolehmainen et al. | 600/585 |
| 6,004,280 A * | 12/1999 | Buck et al. | 600/585 |
| 6,165,163 A * | 12/2000 | Chien et al. | 604/523 |
| 6,346,072 B1 * | 2/2002 | Cooper | 600/102 |
| 6,398,776 B1 * | 6/2002 | Sekino et al. | 604/524 |
| 6,896,671 B2 * | 5/2005 | Vitullo et al. | 604/526 |
| 2003/0191451 A1 * | 10/2003 | Gilmartin | 604/527 |
| 2003/0193190 A1 * | 10/2003 | Werth | F16L 33/225 285/243 |
| 2003/0195426 A1 * | 10/2003 | White et al. | 600/463 |
| 2004/0093061 A1 * | 5/2004 | Acosta | A61F 2/915 623/1.11 |
| 2004/0181208 A1 * | 9/2004 | Poole | 604/527 |
| 2005/0021018 A1 * | 1/2005 | Anderson et al. | 606/28 |
| 2005/0085693 A1 * | 4/2005 | Belson | A61B 1/005 600/146 |
| 2005/0228222 A1 * | 10/2005 | Furumi | A61B 1/0011 600/101 |
| 2005/0273149 A1 * | 12/2005 | Tran et al. | 623/1.11 |
| 2005/0288434 A1 * | 12/2005 | Sugiura et al. | 525/70 |
| 2006/0025753 A1 * | 2/2006 | Kubalak | A61M 25/0017 604/544 |
| 2006/0129091 A1 * | 6/2006 | Bonnette | A61B 17/22 604/93.01 |
| 2007/0207186 A1 * | 9/2007 | Scanlon et al. | 424/424 |
| 2007/0208300 A1 * | 9/2007 | Pravong | A61M 1/008 604/96.01 |
| 2007/0221230 A1 * | 9/2007 | Thompson | A61B 17/12022 128/207.15 |
| 2009/0012500 A1 * | 1/2009 | Murata et al. | 604/525 |

* cited by examiner

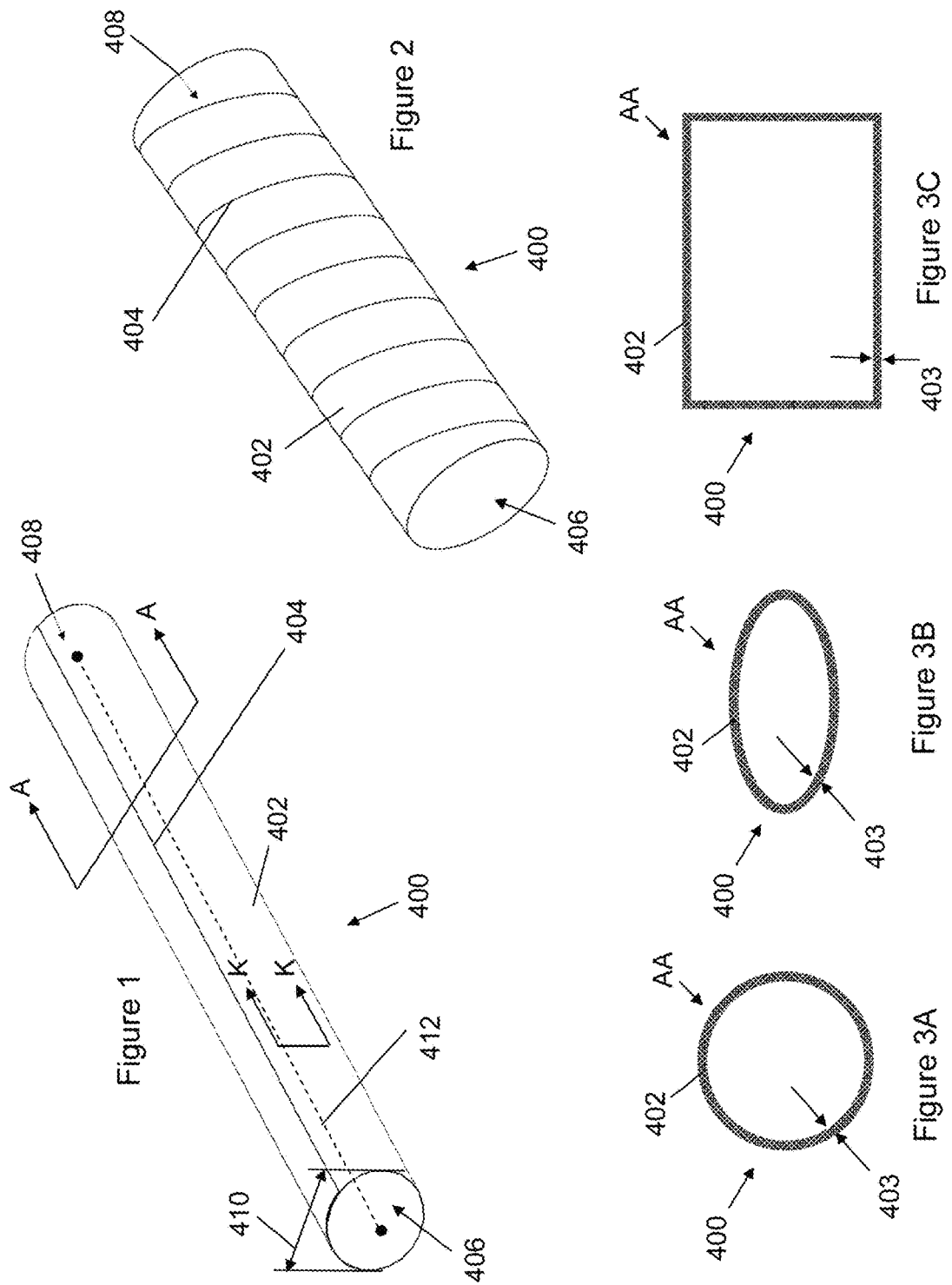

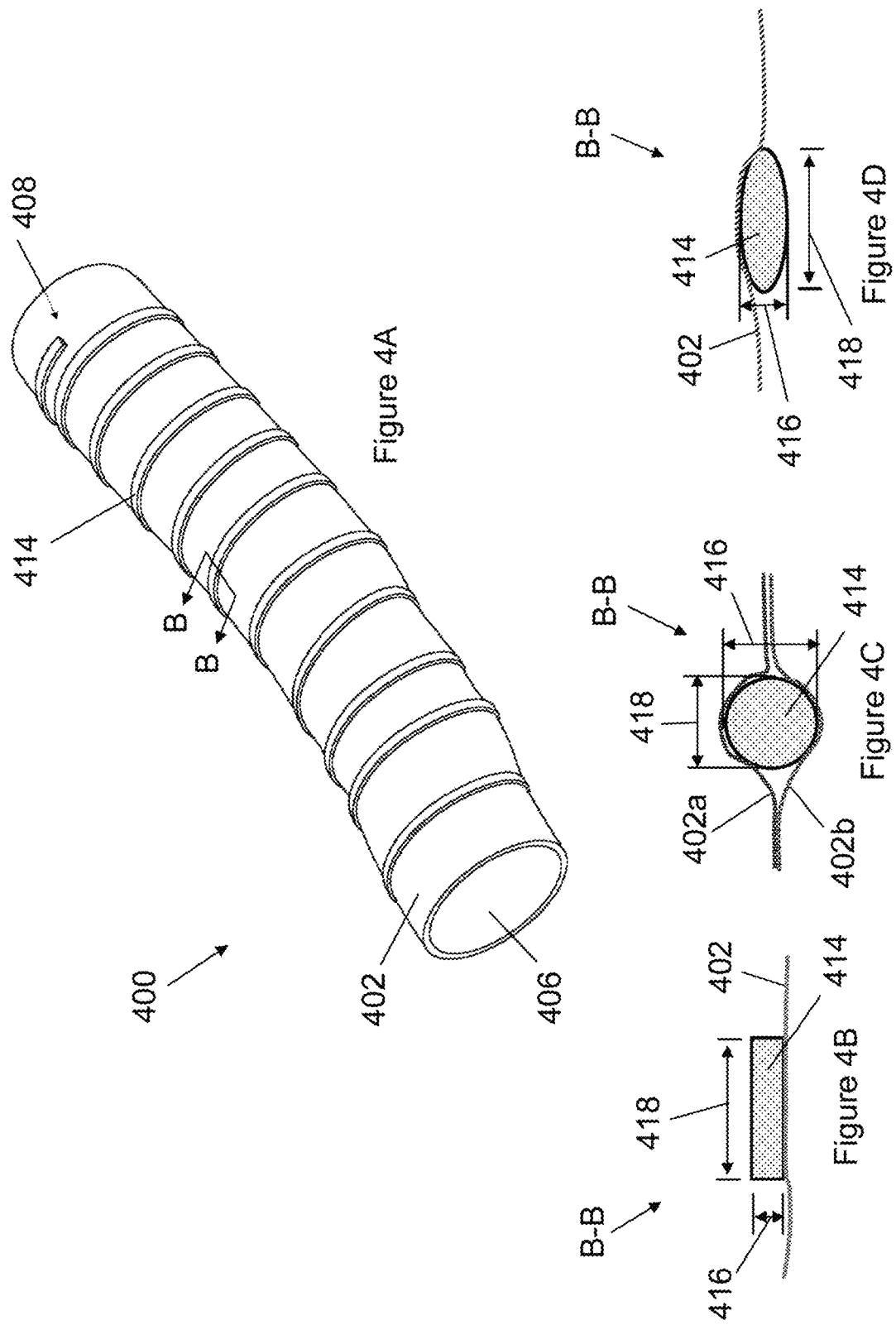

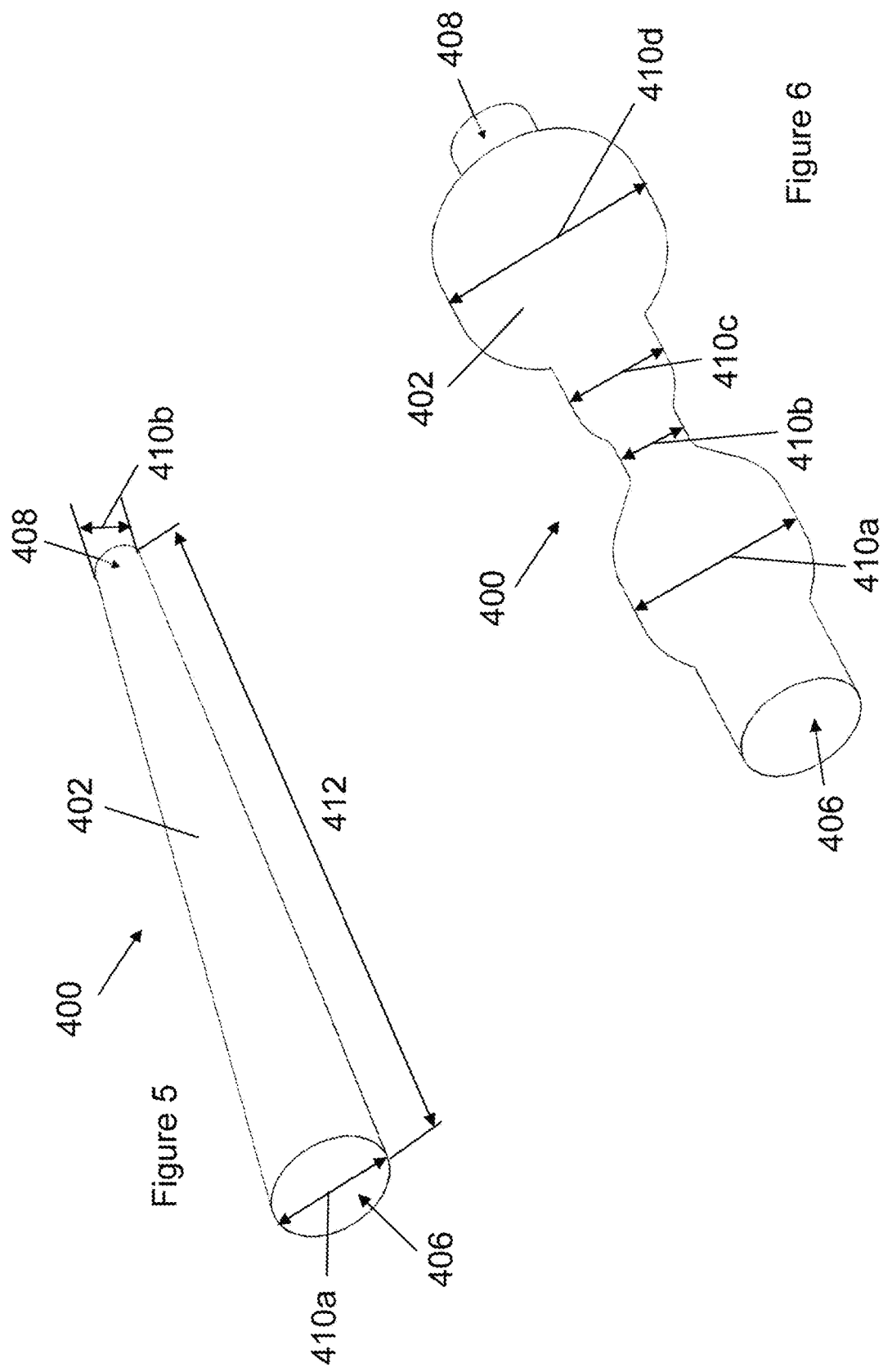

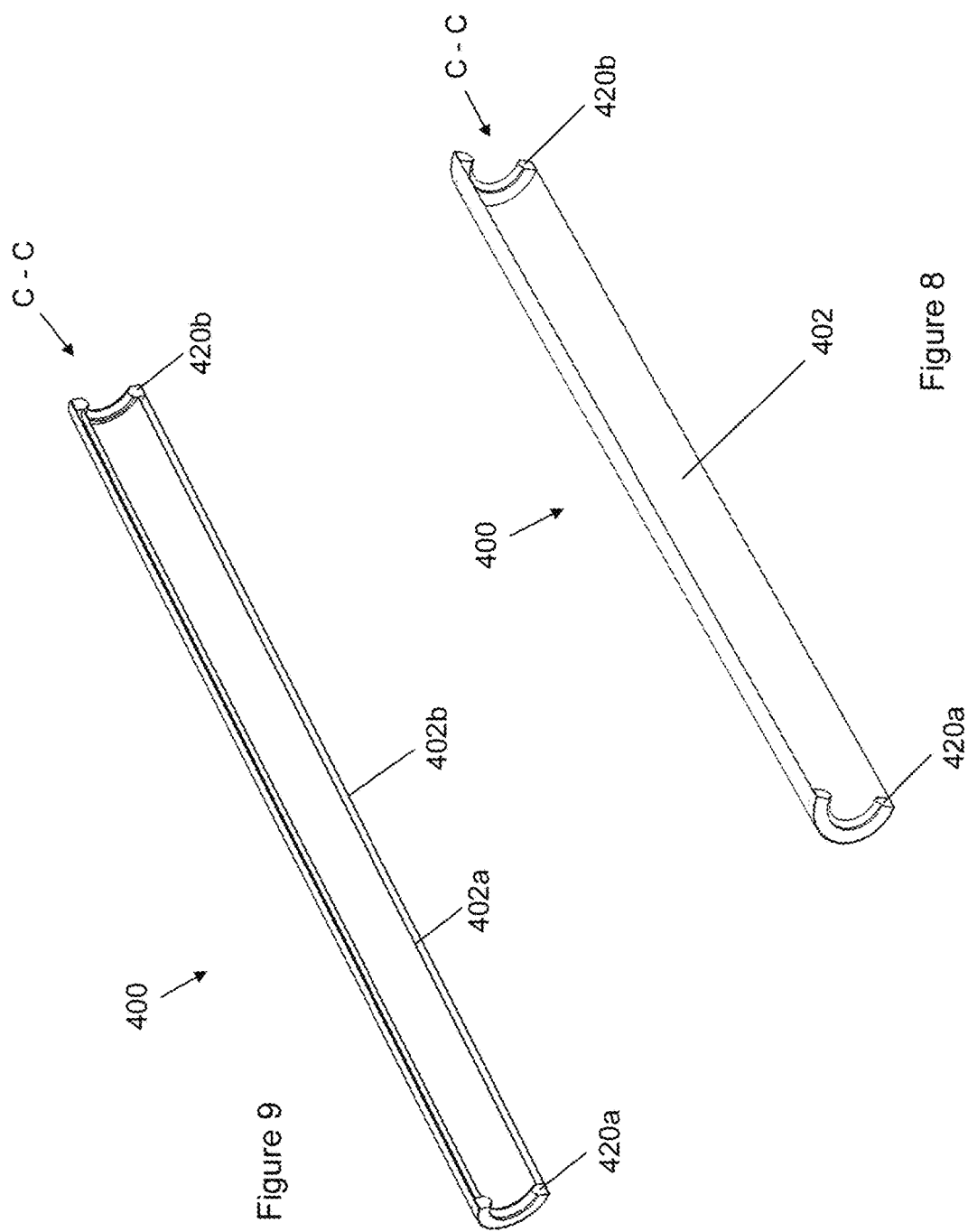

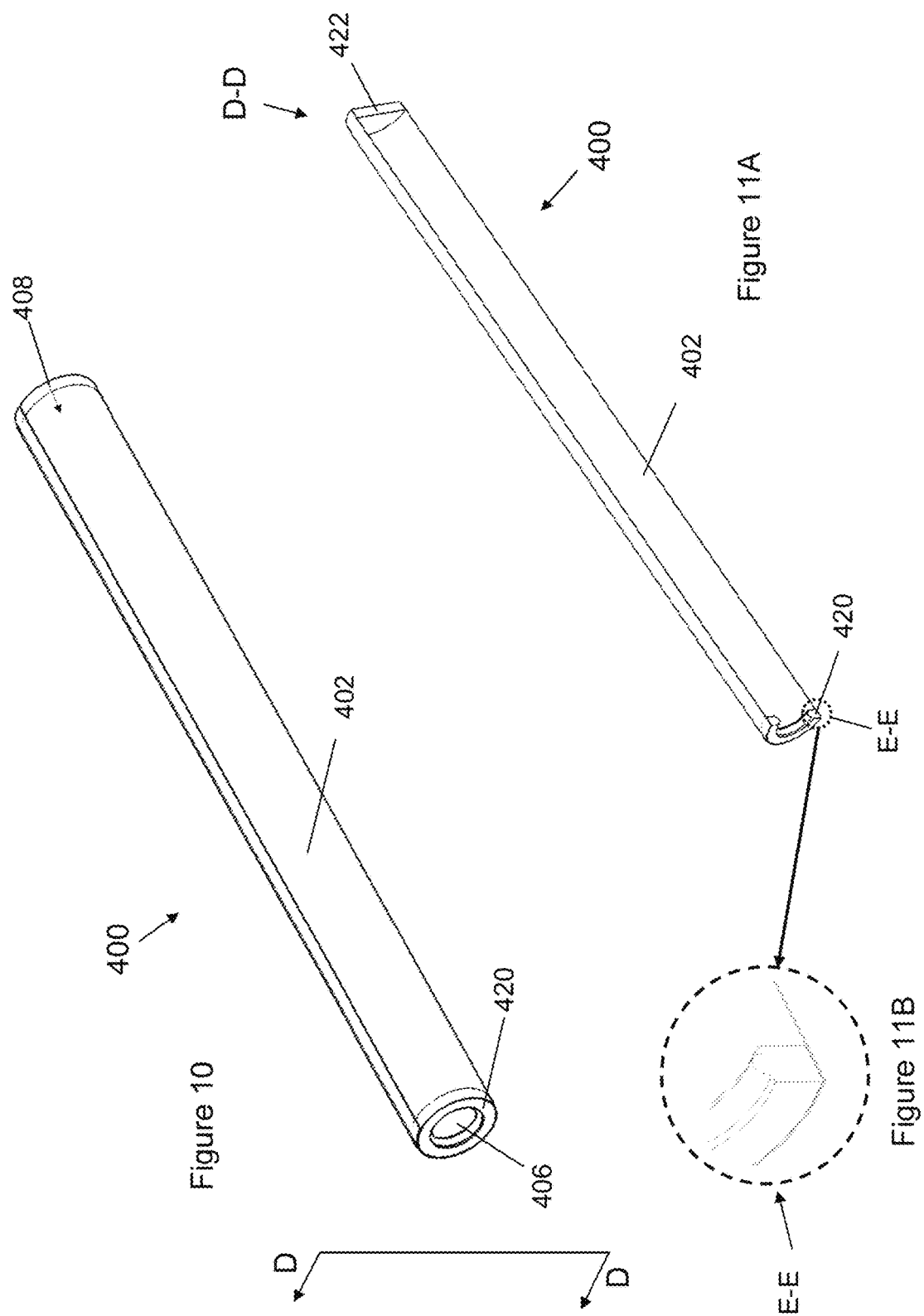

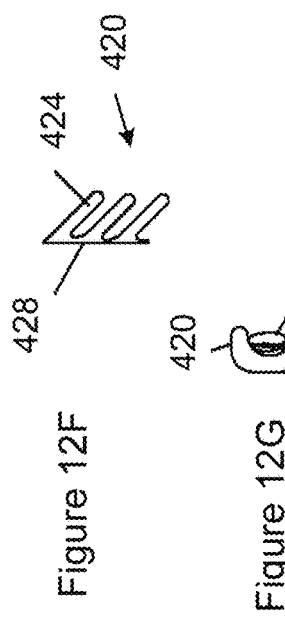
Figure 12A
Figure 12B
Figure 12C
Figure 12D
Figure 12E
Figure 12F
Figure 12G

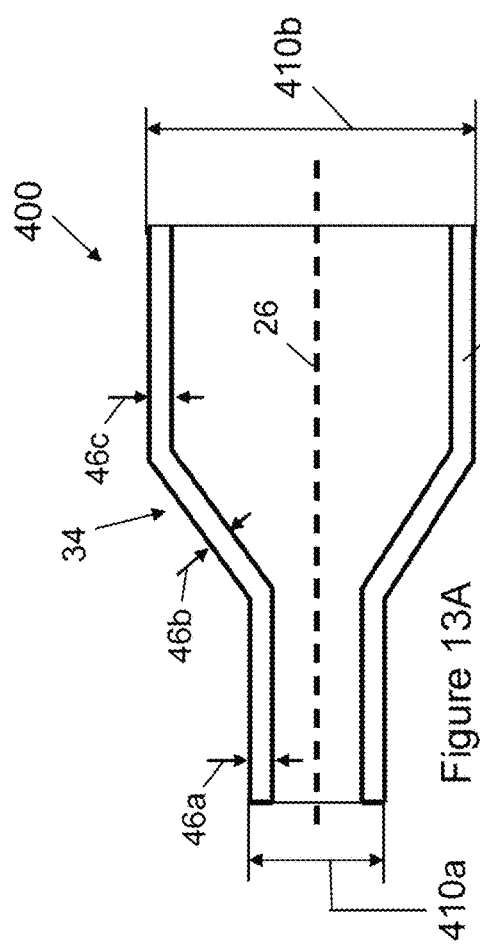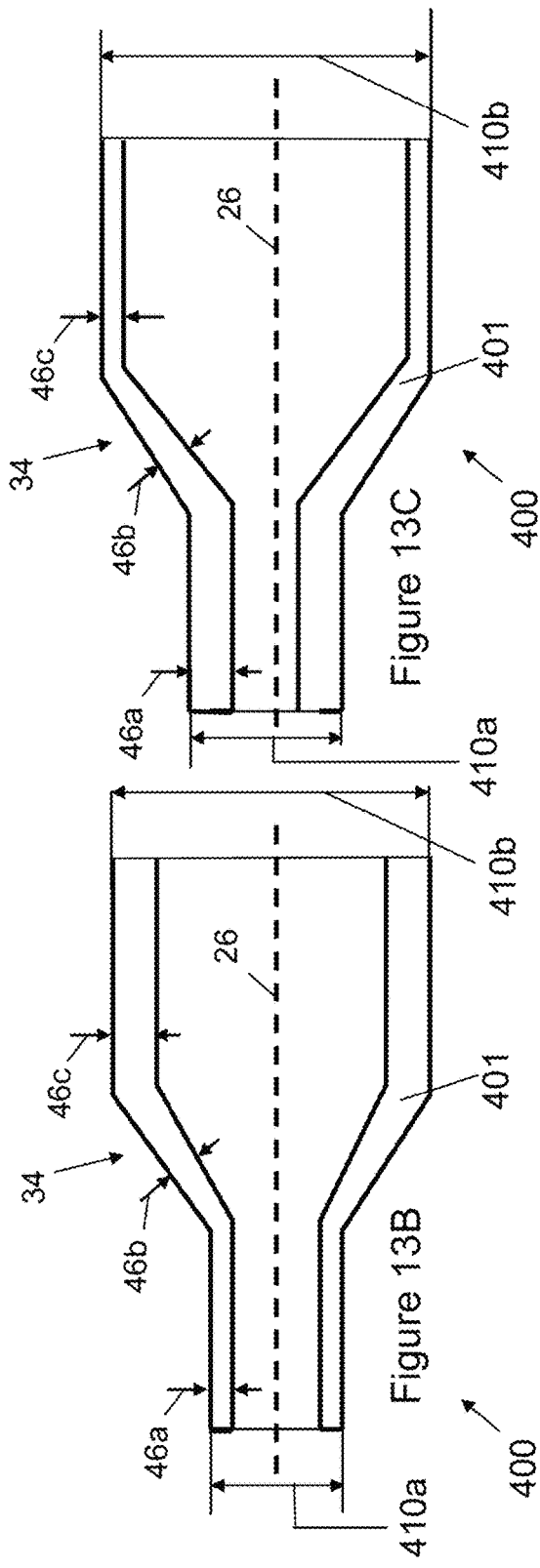
Figure 13A  Figure 13B  Figure 13C

Film Materials

| Type | Sample Manufacturer or Supplier |
|---|---|
| Co-Polyamide | Deerfield Urethane, USA |
| Co-Polyester | Deerfield Urethane, USA |
| ECTFE | Saint-Gobain, France |
| FEP (Fluoroethylene-propylene) | DuPont, USA |
| Kapton | DuPont, USA |
| HDPE | Dow Chemical, USA |
| LDPE | Lyondell Chemical, USA |
| Mylar / PET (Polyethylene Terephthalate) / Polyester | DuPont, USA |
| Nylon | Honeywell, USA |
| PEEK | Victrex, UK |
| PEN (Polyethylene Naphthalate) | DuPont, USA |
| Tedlar (PVF) | DuPont, USA |
| Thermoplastic Polyurethane (TPU) | Deerfield Urethane, USA |
| Vectran (LCP (Liquid Crystal Polymer)) | Hoechst-Celanese, USA |
| Solef | Solvay, Italy |

Figure 16

Reinforcement material

| Type | Sample Manufacturer or Supplier |
|---|---|
| Vectran | Hoechst-Celanese, USA |
| PBO | Dow Chemical, USA |
| Spectra | Allied Signal, USA |
| Conex | Teijin, Japan |
| Dyneema | Teijin, Japan |
| Technora | Teijin, Japan |
| Dacron | DuPont, USA |
| Polyester | Hoechst-Celanese, USA |
| Compet | Allied Signal, USA |
| Nylon | DuPont, USA |
| PEEK | ICI-Fiberite, USA |
| PPS | Phillips Petroleum, USA |
| Boron Fiber | AVCO-Textron, USA |
| Ceramic Fiber | AVCO-Textron, USA |
| Kevlar | DuPont, USA |
| Inorganic Carbon/Carbon Fiber | Hercules Inc., USA |
| Inorganic Silicon/high strength fiberglass | Owens Corning Fiber, USA |
| Organic Polymer/Aramid | DuPont, USA |
| Twaron | Teijin, Japan |

Figure 17

Adhesive and Matrix Materials

| Type | Sample Manufacturer or Supplier |
|---|---|
| Urethanes | Hysol, USA |
| Polyesters | Thiokol, USA |
| Silicones | Dow Chemical, USA |
| Polypropylene | Honam Petrochemical, South Korea |
| Polyolefins | INEOS, UK |
| ULDPE, VLDPE, LDPE | ExxonMobil, USA |
| Nylon | Ashley Polymers, USA |
| Epoxies | Hysol, USA |
| Pebax | Arkema, USA |
| Tefzel | Dupont, USA |
| EVA | Dupont, USA |
| Solef | Solvay, Italy |

Figure 18

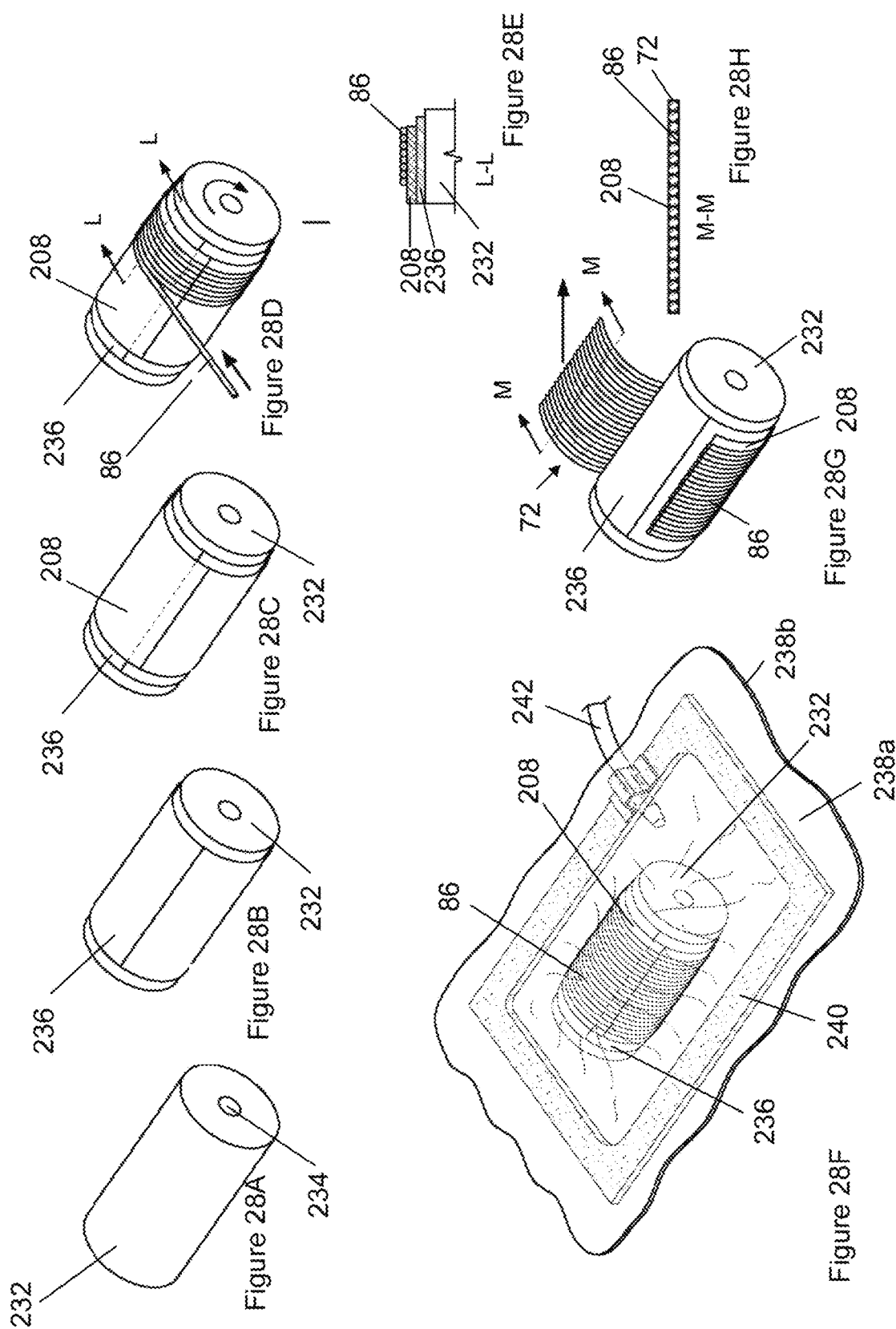

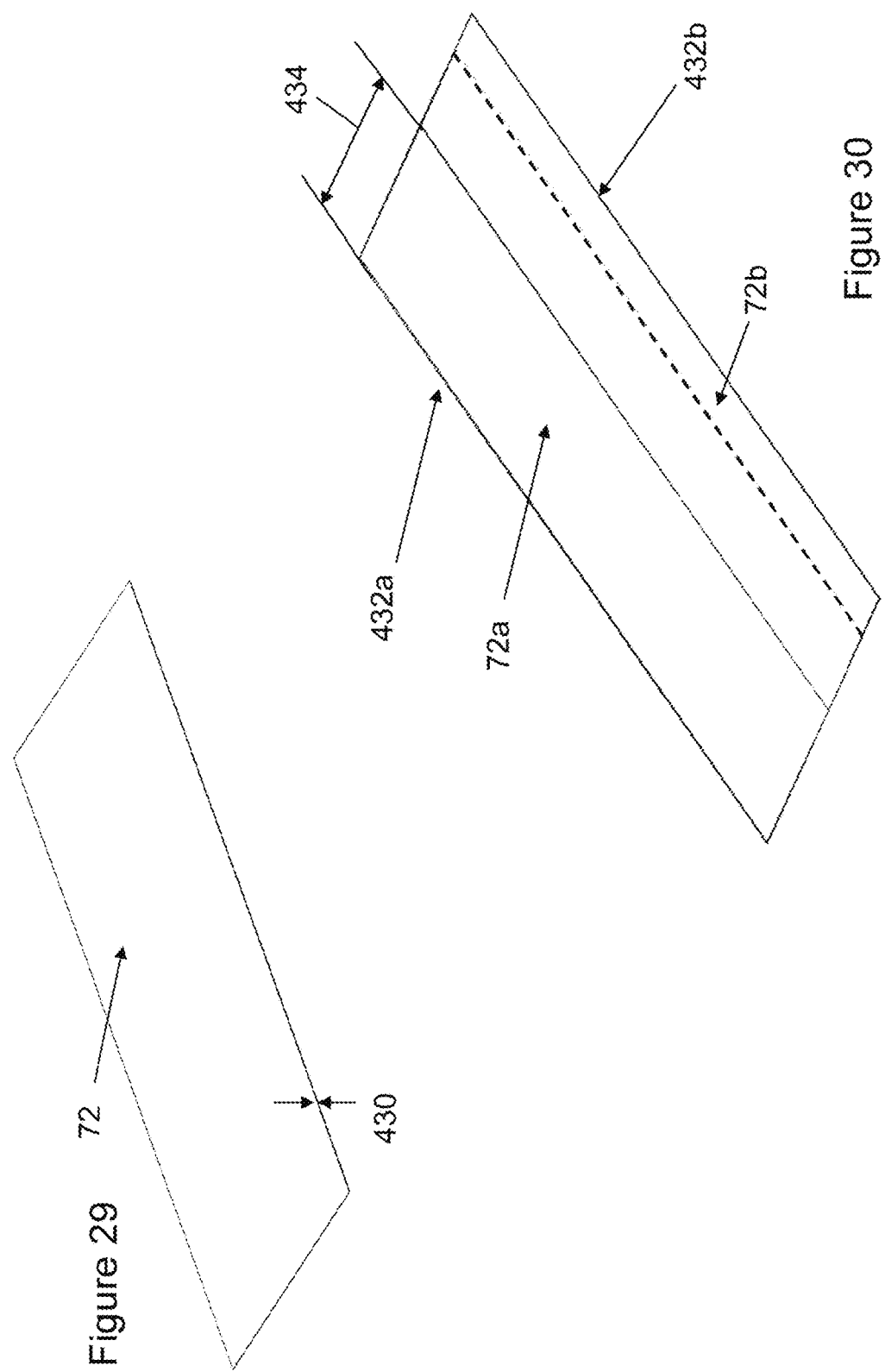

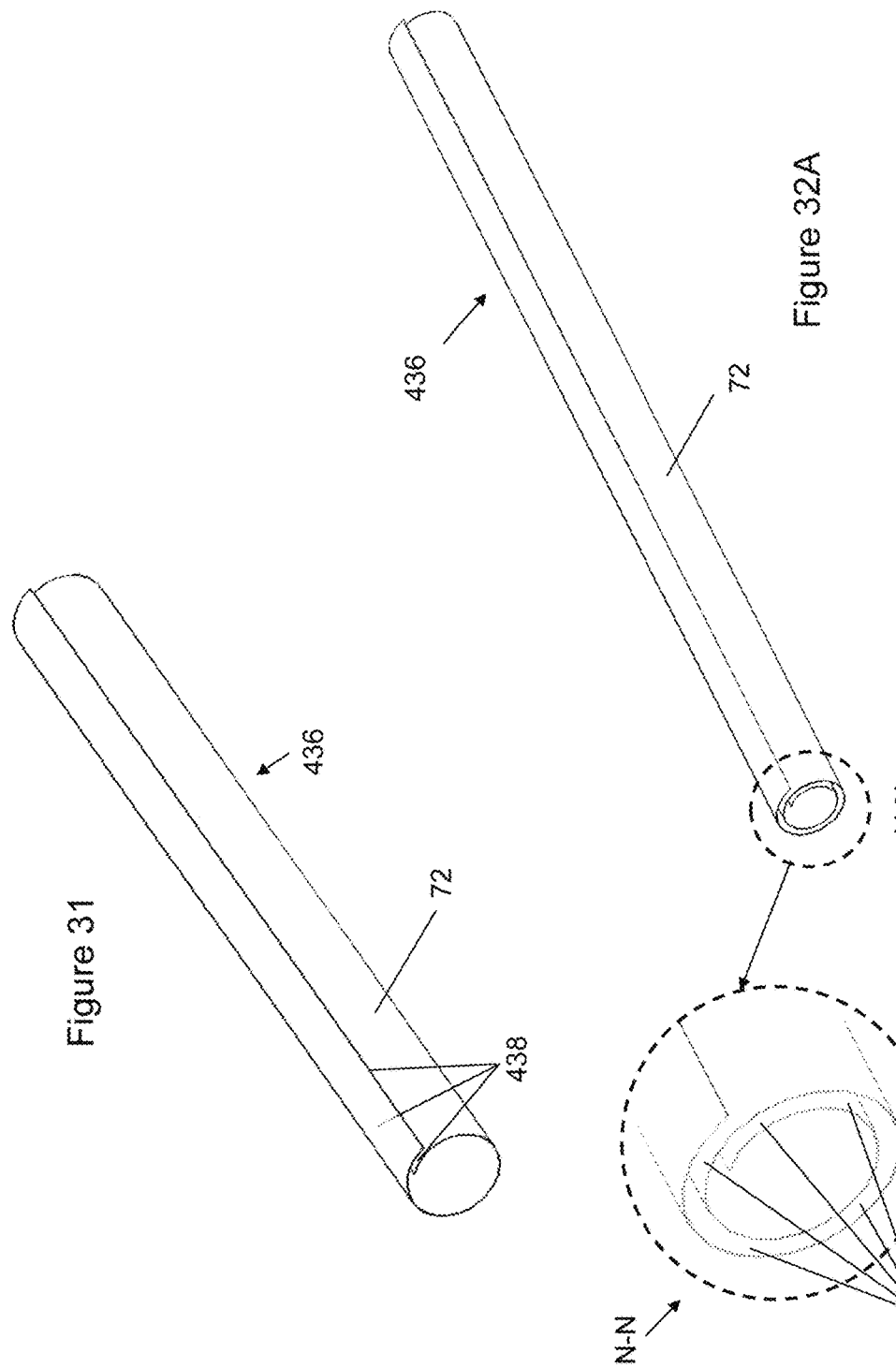

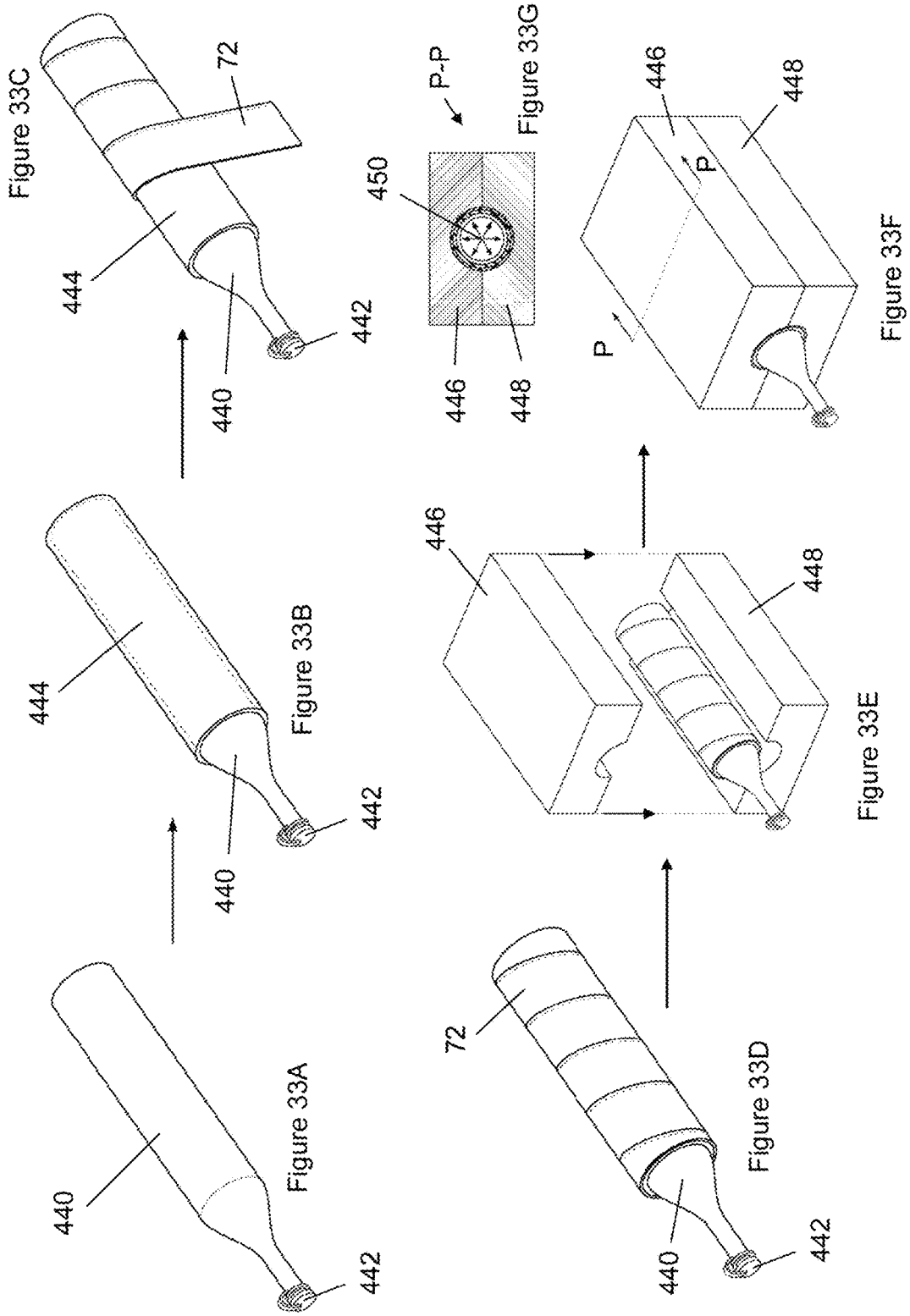

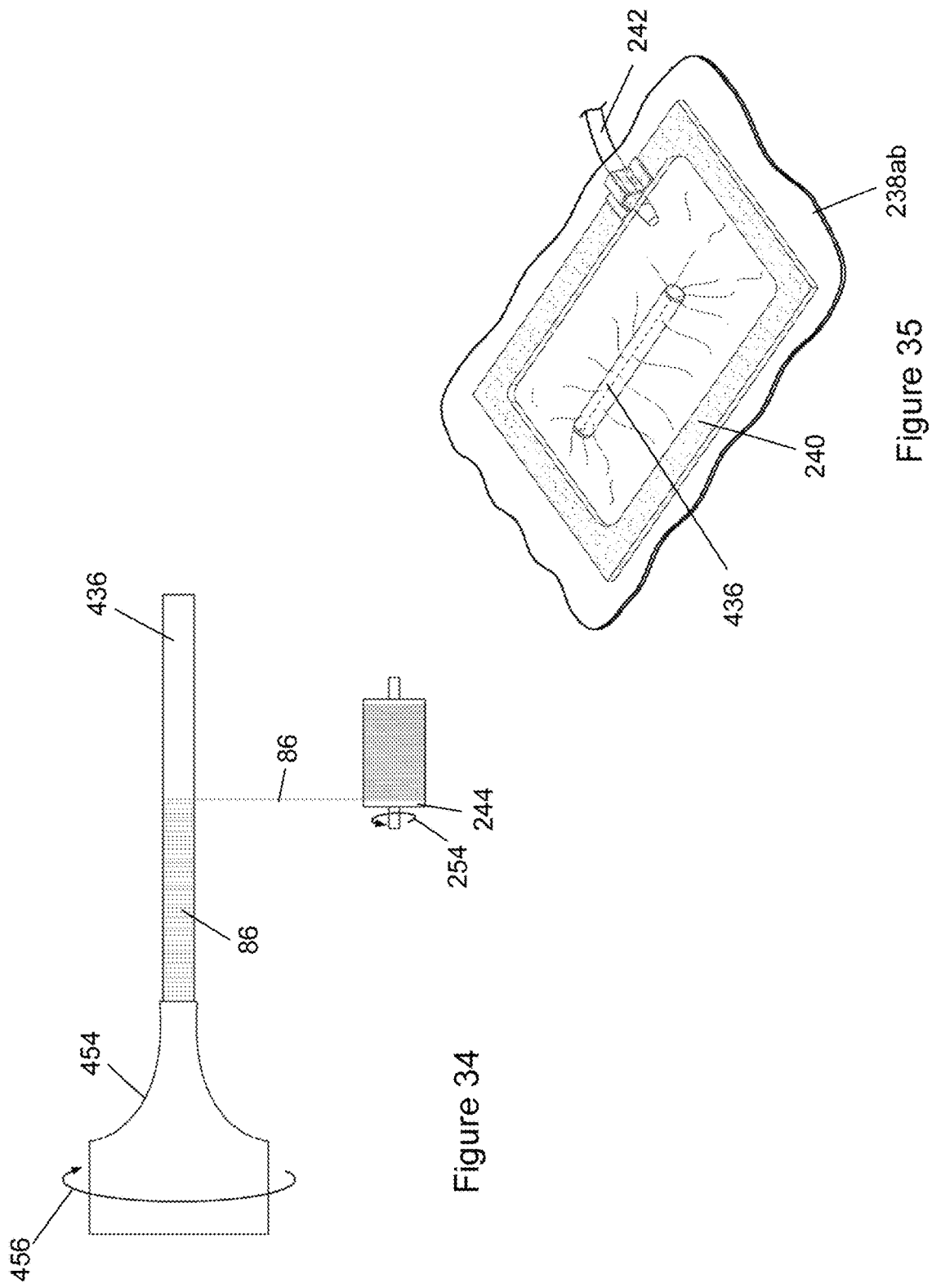

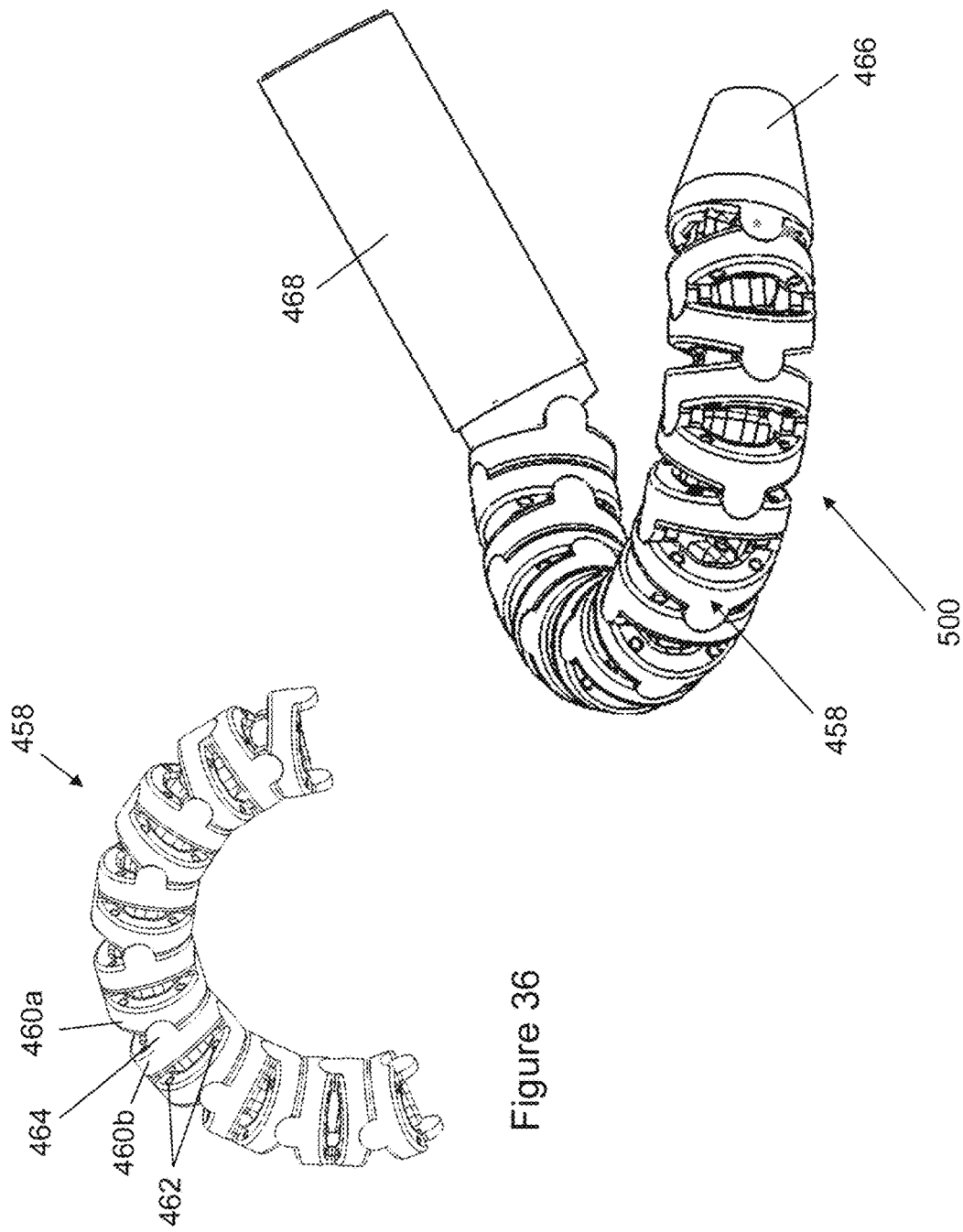

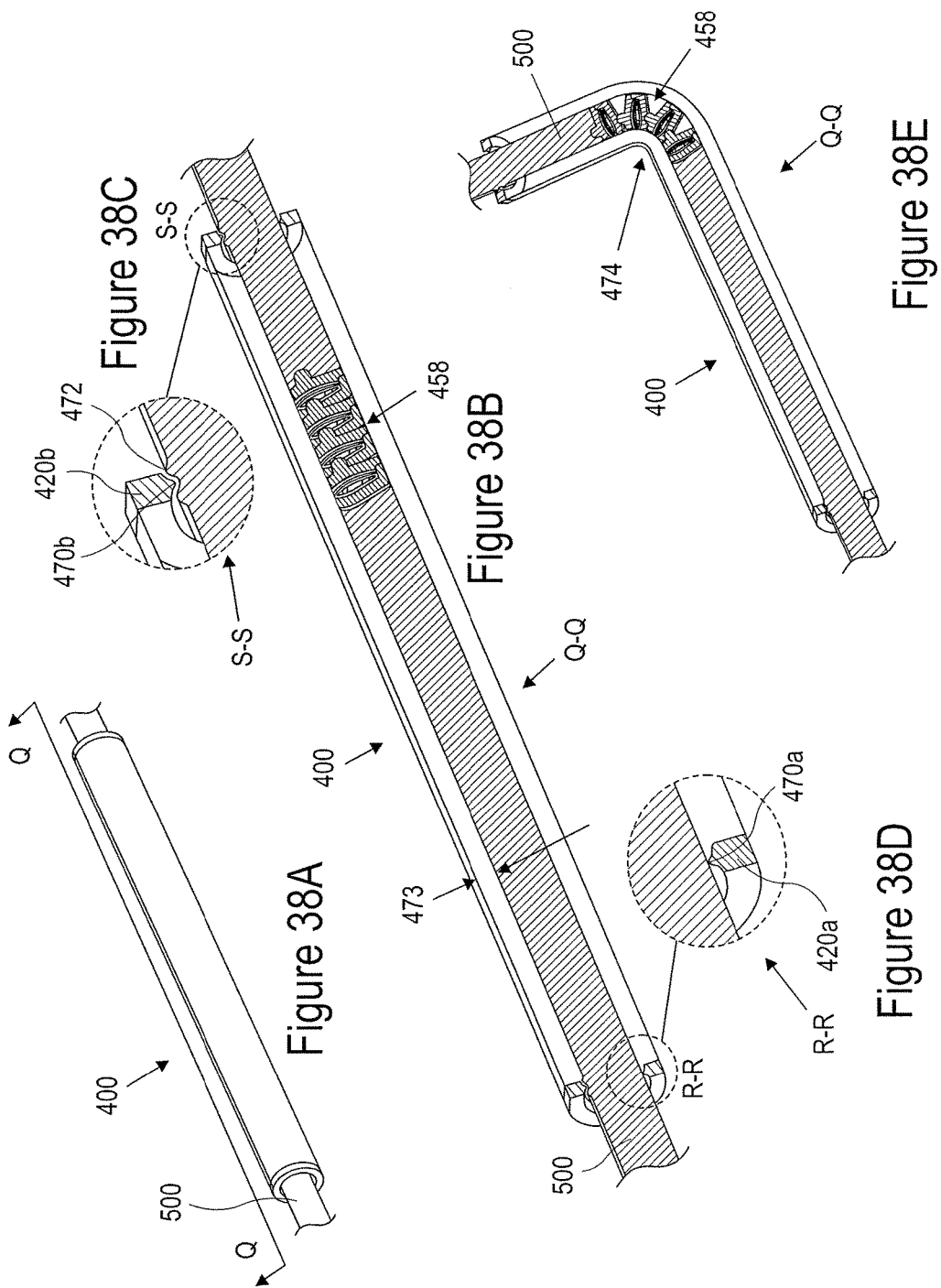

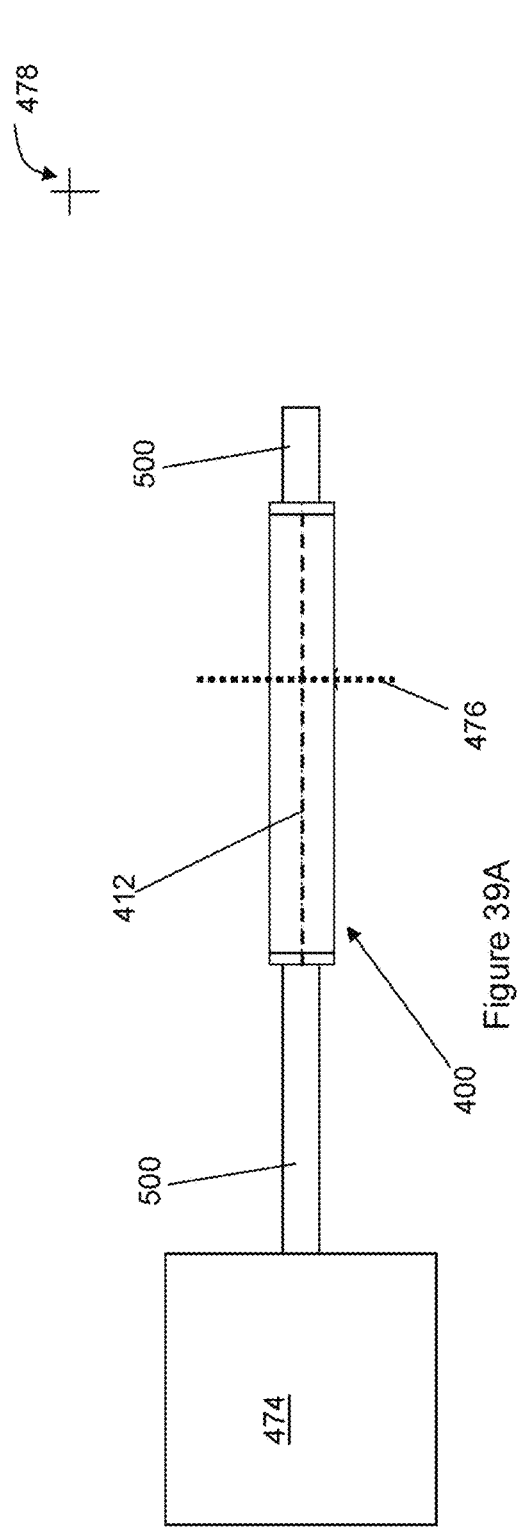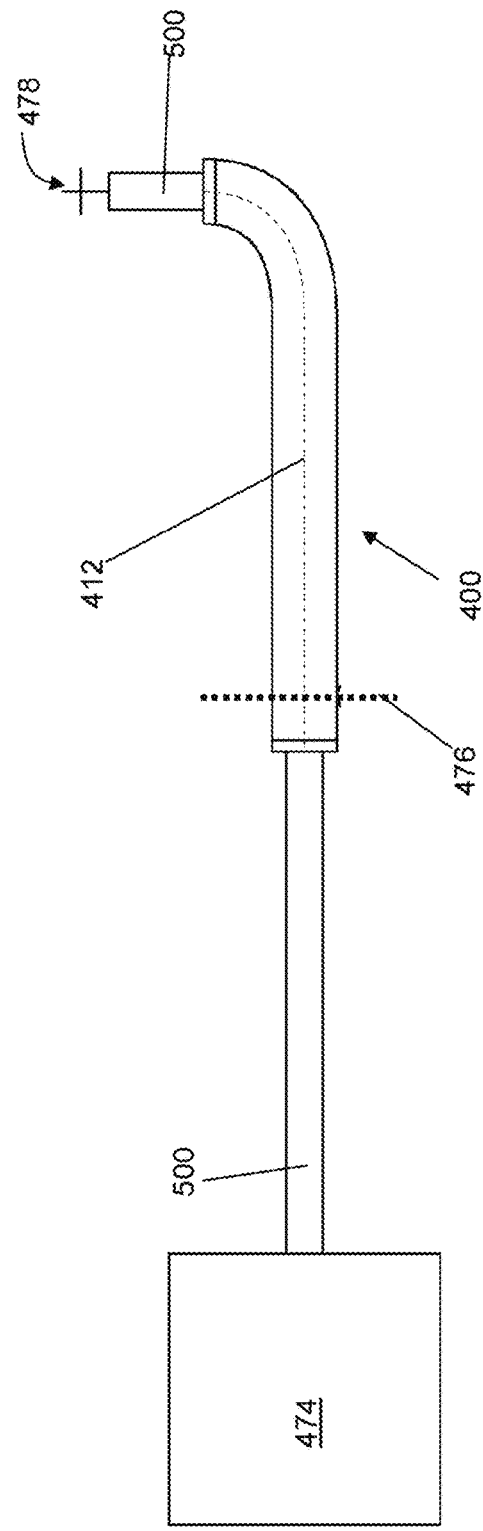

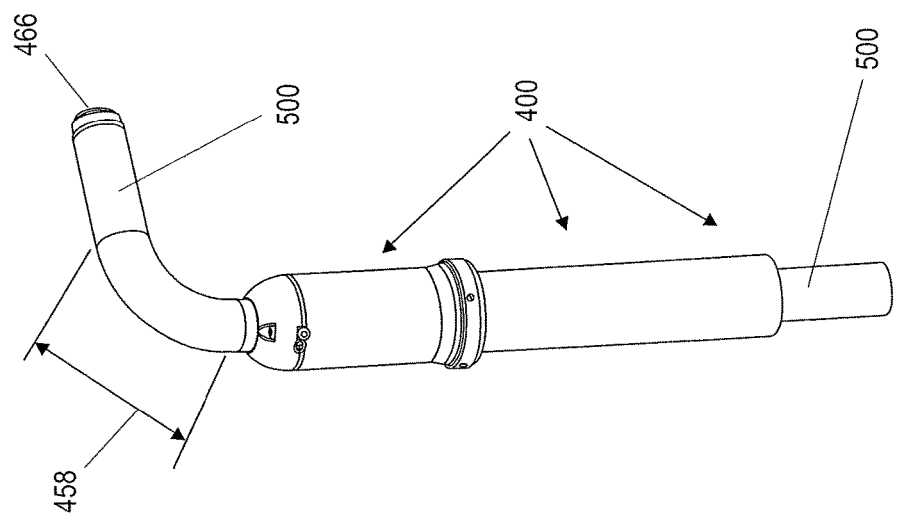
Figure 42
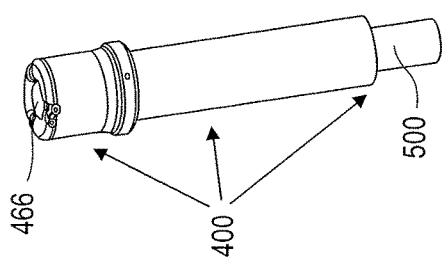
Figure 41A
Figure 41B

SHEATHS FOR MEDICAL DEVICES

CROSS-REFERENCE TO RELATED APPLICATIONS

This application is a continuation in-part of U.S. patent application Ser. No. 12/512,878, filed 30 Jul. 2009, which is a continuation of PCT Application No. US2008/052535, filed 30 Jan. 2008, which claims priority to U.S. Provisional Application Nos. 60/887,319, filed 30 Jan. 2007; 60/887,323, filed 30 Jan. 2007; and 60/949,219, filed 11 Jul. 2007; and is a continuation-in-part of U.S. patent application Ser. No. 12/512,809, filed 30 Jul. 2009, which is a continuation of PCT Application No. US2008/052542, which claims priority to U.S. Provisional Application Nos. 60/887,319, filed 30 Jan. 2007; 60/887,323, filed 30 Jan. 2007; and 60/949,219, filed 11 Jul. 2007; and is a continuation of PCT Application No. US2009/41637, filed 24 Apr. 2009, which claims priority to U.S. Provisional Application No. 61/125,720, filed 27 Apr. 2008; and is a continuation-in-part of U.S. application Ser. No. 12/477,005, filed 2 Jun. 2009, which claims priority to U.S. Provisional Application Nos. 61/057,986, filed 2 Jun. 2008; 61/086,739, filed 6 Aug. 2008; 61/105,385, filed 14 Oct. 2008, and 61/205,866, filed 22 Jan. 2009; and is a continuation-in-part of U.S. application Ser. No. 12/477,048, filed 2 Jun. 2009, which claims priority to U.S. Provisional Application Nos. 61/057,986, filed 2 Jun. 2008; 61/086,739, filed 6 Aug. 2008; 61/105,385, filed 14 Oct. 2008, and 61/205,866, filed 22 Jan. 2009; and claims priority to 61/086,739, filed 6 Aug. 2008, all of which are incorporated by reference herein in their entireties.

BACKGROUND OF THE INVENTION

1. Field of the Invention

This invention relates to the design and manufacture of high performance sheaths for use in medicine and other applications. These sheaths may be placed over devices intended for the exploration and modification of luminal cavities. The devices may be medical devices used to explore and modify the body.

2. Description of the Related Art

Devices used to explore and modify luminal cavities may become contaminated by their surroundings. A medical device used in the body may become contaminated with material from the patient's body. The medical device may be disposed of after use in a single patient. Alternately, the medical device may be cleaned after each procedure.

Alternately, the medical device may be covered, or partially covered, with a sheath that protects, or partially protects, the medical device from contamination. This sheath may then be disposed of after each procedure. This sheath may be an integral or permanent part of the medical device. The medical device may need some or no cleaning.

Current sheaths are generally simple, homogenous polymer structures. Because they are made from a single material, they may represent a compromise between all the competing engineering requirements that sheath may have. In many applications, these compromises harm the efficacy, cost, or efficiency of the medical procedure in which the medical device is being used. What is needed is a sheath that can be constructed in such a way as to selectively incorporate whatever properties are required for the application.

SUMMARY OF THE INVENTION

A device is disclosed for therapeutic and/or diagnostic use in or on a patient's body. The device can have a sheath and a tool. The sheath can have a laminate. The laminate can have reinforcement fibers. The sheath can have a sheath length measured from a distal end of sheath to a proximal end of the sheath. The tool can be at least partially within the sheath. The tool can be attached to the sheath.

The tool can have a first proximal position and a second distal position. The sheath length when the tool is in the first proximal position can be substantially equal to the sheath length when the tool is in the second distal position.

The sheath can have a reinforcement member. The reinforcement member can be more rigid than the laminate. The reinforcement member can be substantially helical. The reinforcement member can be plastic, metal, any other material disclosed herein, or combinations thereof.

The tool can be releasably attached to the sheath.

The device can have a robotic system for therapeutic and/or diagnostic use. The tool can be part of or attached to the robotic system. The sheath can have a fluid-tight seal to the tool.

A further device for therapeutic and/or diagnostic use in or on a patient's body is disclosed. The device can have a sheath and a tool. The sheath can have a laminate having reinforcement fibers. The tool can be at least partially within the sheath. The tool can be fixedly attached to the sheath.

The tool can have a sheathed tool length measured along the length of tool within the sheath. The tool can have a first proximal position and a second distal position. The sheathed tool length in the first proximal position can be less than about 10% different (i.e., more or less) than the sheathed tool length in the second distal position.

A method is described for using a tool in or on a patient's body. The method can include attaching a distal end of a fiber-reinforced first sheath to a tool. The tool can be radially within the fiber-reinforced first sheath. The method can include sealing the first sheath to the tool. The sealing can include sealing the distal end of the first sheath to the tool. The method can include deploying the tool to a target site in or on a patient's body for therapy and/or diagnostic use. Deploying the tool can include controlling a robotic system to move the tool.

The method can include detaching the first sheath from the tool. The method can also include attaching a second sheath to the tool while the first sheath is attached to the tool or after the first sheath is detached and/or removed from the tool.

BRIEF DESCRIPTION OF THE FIGURES

FIG. 1 illustrates a variation of the device.
FIG. 2 illustrates a variation of the device.
FIGS. 3A through 3C are variations of cross-section A-A of FIG. 1.
FIG. 4A illustrates a variation of the device.
FIGS. 4B through 4D are variations of cross-section B-B of FIG. 4A.
FIG. 5 illustrates a variation of the device.
FIG. 6 illustrates a variation of the device.
FIGS. 8 and 9 are variations of cross-section C-C of FIG. 7.
FIG. 10 illustrates a variation of the device.
FIG. 11A is a variation of cross-section D-D of FIG. 10.
FIG. 11B is a close up view of circle E-E of FIG. 11A.
FIGS. 12A through 12G illustrate variations of a seal.
FIGS. 13A through 13C are cross-sectional views of a length of variations of the device.

FIGS. 16 through 18 are tables listing film materials, reinforcement materials, and adhesive and matrix materials, respectively.

FIGS. 28A through 28H illustrate a method of making fiber tape.

FIGS. 29 through 32A illustrate a variation of a method for manufacturing the device.

FIG. 32B illustrates a closeup of circle N-N of FIG. 32A.

FIGS. 33A through 33G illustrate a variation of a method for manufacturing the device.

FIG. 34 illustrates a variation of a method for applying fiber to a sheath.

FIG. 35 illustrates a variation of a method for curing or compacting a sheath.

FIGS. 36 and 37 illustrate a variation of a medical device.

FIG. 38A illustrates a variation of a method of using the device with a medical device.

FIG. 38B illustrates a variation of a cross section Q-Q of FIG. 38A.

FIG. 38C illustrates a variation of a closeup S-S of FIG. 38B.

FIG. 38D illustrates a variation of a closeup R-R of FIG. 38B.

FIG. 38E illustrates a variation of the cross section shown in FIG. 38B in which the articulating section of the medical device is bent at about 90 degrees.

FIGS. 39A and 39B illustrate a variation of a method of using a variation of the device in the body.

FIG. 41A illustrates a variation of the device attached to a medical device.

FIG. 41B illustrates a variation of the device attached to a medical device which is articulated into 90 degree bend.

FIG. 42 illustrates a variation of the device attached proximal to the articulating section of a medical device.

DETAILED DESCRIPTION

Figure 7:
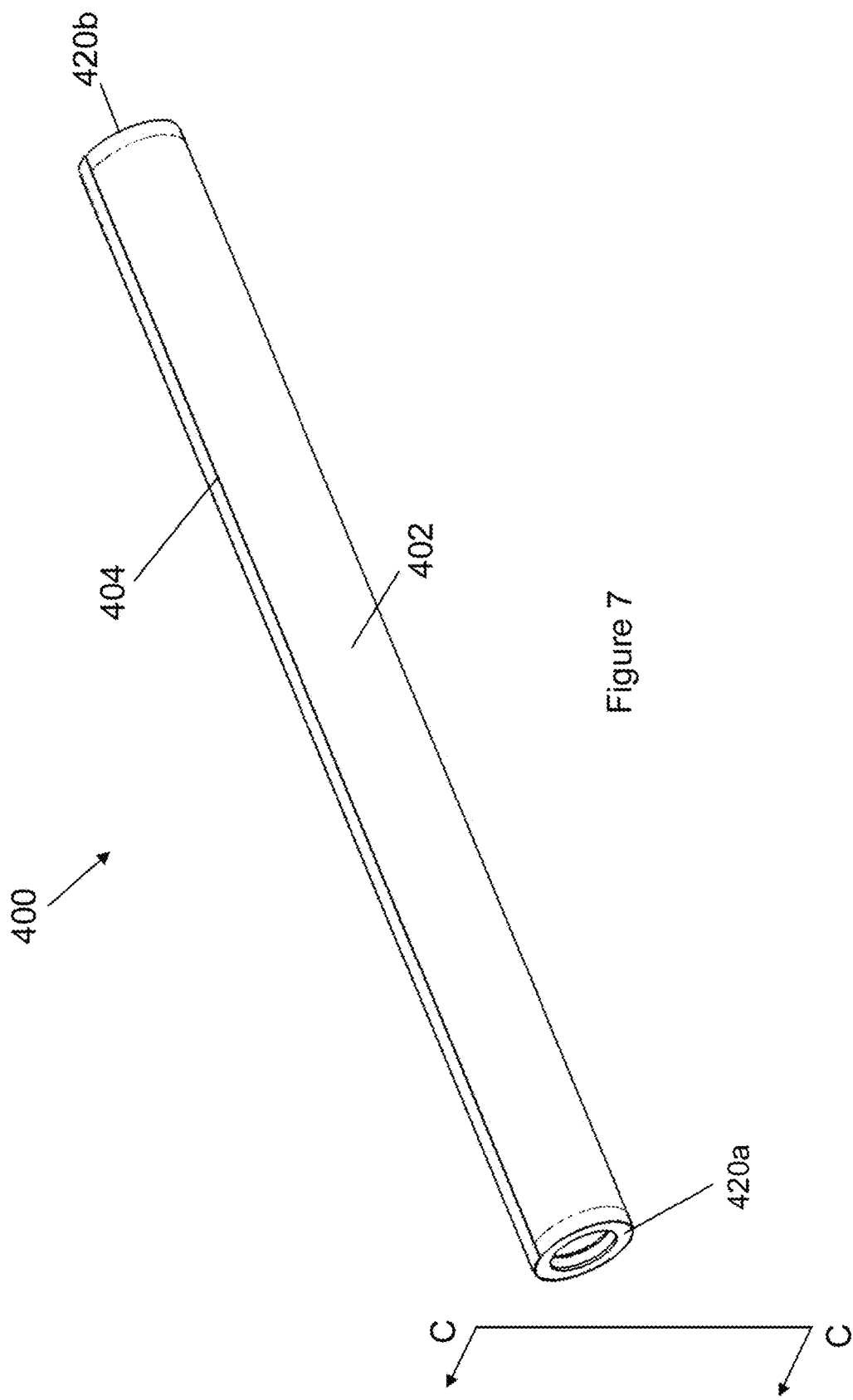
FIG. 7 illustrates a variation of the device.

FIG. 1 shows a sheath 400. The sheath may have or be one or more tubes 402. Tube 402 may have a seam 404 running down the long axis of the tube 402. The wall of tube 402 may be substantially leak-tight or fluid-tight. Tube 402 may have an open proximal end 406 and/or an open distal end 408. Proximal end 406 may be closed. Distal end 408 may be closed. Tube 402 may have a substantially constant diameter 410 and longitudinal length 412. Longitudinal sheath length 412 can be measured along the of the longitudinal axis of the sheath wherein the longitudinal axis follows the centerline of the sheath at all points Diameter 410 can be from about 0.1 inches to about 4 inches. Longitudinal sheath length 412 can be from about 2 inches to about 10 feet.

FIG. 2 shows a variation of sheath 400. Seam 404 can form a spiral configuration on the outer surface of tube 402. The tube 402 can have a flat ribbon of material that is helically wrapped and sealed at the seam 404.

FIGS. 3A, 3B and 3C show variations of a cross section of sheath 400 taken at line A-A. FIG. 3A illustrates that the tube 402 can have a circular cross section. FIG. 3B illustrates that the tube 402 can have an elliptical cross section. FIG. 3C illustrates that the tube 402 can have a square or rectangular cross section.

The tube 402 may have a tube wall 401 and a wall thickness 403. The wall thickness 403 can be less than about 25 μm (0.98 mil). The wall thickness 403 can be from about 25 μm (0.98 mil) to about 500 μm (18.6 mil), more narrowly from about 50 μm (2 mil) to about 300 μm (11.8 mil), for example about 75 μm (3.0 mil) or about 100 μm (4 mil).

Tube wall 401 and tube 402 may be highly flexible, foldable articles. Tube wall 401 may have a high strength. For example, the tube wall 401 may have an ultimate strength of greater than about 138 MPa (20 Ksi), more narrowly greater than about 276 MPA (40 Ksi), yet more narrowly greater than about 414 MPa (60 Ksi).

The sheath 400 can have an unsupported burst pressure. The unsupported burst pressure is the pressure at which the sheath 400 ruptures when inflated in free air without any external constraint on the walls at about 1 atm external pressure and about 20° C. temperature. If the proximal end 406 is open, this end must first be capped to run this test. If the distal end 408 is open, this end must first be capped to run this test. The unsupported burst pressure can be greater than about 150 psi. For example, the unsupported burst pressure can be from about 1,400 kPa (200 psi) to about 10,000 MPa (1,500 psi). More narrowly, the burst pressure can be from about 3,500 kPa (500 psi) to about 6,000 kPa (900 psi). For example, the burst pressure can be about 3,500 kPa (500 psi), about 5,200 kPa (750 psi), about 7,000 (1,000 psi), about 10,000 kPa (1,500 psi), or higher than 10,000 kPa (1500 psi).

The sheath 400 can be non-compliant or inelastic. The sheath 400 can have a failure strain of less than 0.30, more narrowly less than 0.20, more narrowly less than 0.10, yet more narrowly less than 0.05. A non-compliant sheath can have a failure strain of less than 0.30.

The failure strain of the sheath is the difference between the balloon outer diameter 410 when the balloon is inflated to 100% of the burst pressure and the balloon outer diameter when the balloon is inflated to 5% of the burst pressure (i.e., to expand from a deflated state without stretching the wall material) divided by the 100% pressure diameter.

For example, the burst pressure of the sheath 400 can be greater than about 3,500 kPa (500 psi) and have an outer diameter of about 17 mm and a wall thickness of less than about 100 μm with a failure strain of less than about 0.10, for example less than about 0.05.

The reinforced tube wall 401 may have a high tear strength as compared to traditional polymers. Tear strength can correlate to puncture strength and toughness. For example, in a Mod Mil-C-21189 10.2.4 tear test, a specimen is created. That specimen has a width, a height, and thickness. A slit is made in the sample parallel to the width, mid-way along its height. The slit is then pulled to initiate tear at the corners of the slit. The Mod Mil-C-21189 10.2.4 tear test gives resultant data in tensile pounds force (lbf). For the test to be meaningful as a comparison between two material samples, it should be done on a thickness-comparable basis. A nylon 12 sheath material at about 0.0055 in. thickness failed the test at a mean tensile load of 25 lbf. The sheath wall of about 0.005 in. failed at a mean tensile value of 134 lbf.

In an ASTM D-3039 tensile test, a nylon 12 material at 0.0055 in. thickness, failed at a mean tensile load of 22 lbf. The sheath wall of about 0.005 in. thickness can have a mean tensile failure value of about 222 lbf.

The sheath 400 may have a high dielectric strength. For instance, it may have a dielectric strength greater than 1000 volts per mil (i.e., 0.001 in.), for example greater than 2500 volts per mil, also for example greater than 5000 volts per mil.

The sheath 400 can be made from a material that can be resistant to chemicals, for example on the outside surface of the sheath 400. For instance, a material may be chosen that is resistant to bone cement (e.g., methyl methacrylate or polymethyl methacrylate)

FIG. 4A shows a variation of sheath 400 with a tube 402 and a reinforcement member 414. The reinforcement member 414 may form a spiral. The reinforcement member 414 may be attached to the tube 402. The reinforcement member 414 may be a helical spring. The reinforcement member 414 can be more rigid than the laminate of the wall of the tube. The reinforcement member 414 can be made from a plastic, metal, any material described herein, or combinations thereof.

FIGS. 4B, 4C and 4D show several possible cross sectional variations of the reinforcement member 414.

FIG. 4B shows a rectangular cross section of reinforcement member 414 with width 418 and height 416. FIG. 4B shows the reinforcement member 414 attached to the outer wall of tube 402.

FIG. 4C shows a circular cross section of reinforcement member 414 with width 418 and height 416. FIG. 4C shows the reinforcement member 414 placed between tube 402A and tube 402B.

FIG. 4D shows an elliptical cross section of reinforcement member 414 with width 418 and height 416. FIG. 4D shows the reinforcement member 414 attached to the inner wall of tube 402.

Width 418 can be from about 0.001 in. to about 0.100 in., more narrowly from about 0.010 in. to about 0.040 in. Height 416 can be from about 0.0005 in. to about 0.050 in., more narrowly from about 0.002 in. to about 0.010 in.

FIG. 5 shows a variation of sheath 400 with tube 402. Tube 402 may have a first diameter 410a at the proximal tube end 406 and a second diameter 410B at the distal tube end 408. First diameter 410a may be larger than second diameter 410b. The tube diameter may smoothly taper between the proximal and distal ends of the tube 402.

FIG. 6 shows a variation of sheath 400 with tube 402. Tube 402 may have a first diameter 410a, a second diameter 410b, a third diameter 410c and a fourth diameter 410D. The diameters can smoothly vary along the length of the tube.

FIG. 7 shows a variation of sheath 400 with tube 402 and seam 404. Sheath 400 may have a proximal seal 420a and distal seal 420B.

FIG. 8 shows a variation of a cross sectional view of FIG. 7. Sheath 400 is shown with a single tube 402.

FIG. 9 shows a variation of a cross sectional view of FIG. 7. Sheath 400 is shown with a tube 402a and tube 402b. Tube 402a is inside of tube 402b.

FIG. 10 shows a variation of sheath 400. FIG. 11A shows a cross section of FIG. 10. FIG. 11B shows a magnified view of a portion of FIG. 11A. The distal end 408 of sheath 400 may have an endcap 422. Endcap 422 may be located within the inside diameter of tube 402. Endcap 422 may fit over the distal end of a medical device. Endcap 422 may be a clear window. Endcap 422 may make an airtight, circumferential attachment to tube 402. Endcap 422 may contain an adhesive seal, a heat seal, an external band seal or combinations thereof. Endcap 422 may attach to a medical device. The proximal end 406 of the sheath may have a seal 420.

FIG. 12a illustrates a seal 420 having a substantially circular cross-section. FIG. 12b illustrates a seal 420 having a substantially x-shaped cross-section. The seal in FIG. 12b can have four seal anus 424 extending therefrom. FIG. 12c illustrates a seal 420 having a substantially C-shaped cross-section. The seal in FIG. 12c can have two seal arms 424 extending therefrom. FIG. 12d illustrates that seal 420 can be a cup seal. Cup seals can have cantilevered sealing surfaces, which can be lower drag and more compliant against irregular surfaces than o-ring (compression) seals. FIG. 12e illustrates that the seal 420 can have one or more separate seal heads 426 each with a single seal arm extending from the seal head 426. All of the seal arms 424 can all be unidirectional. FIG. 12f illustrates that the seal 420 can have a number of unidirectional seal arms 420 extending from a single backing 428. FIG. 12g illustrates that the seal 420 can have a seal spring 429 inserted into the seal 420 to pressurize the cantilever arms 420 outward.

The seal durometer, material surface friction, squeeze pressure, size, pressure area, and combinations thereof can be varied to modulate desired seal drag. Seal materials can be low durometer to be more compliant and seal with lower forces and lower drag. The seals 420 can have in-seal lubricants. Fluid lubrication can be applied to the seal 420. The seal 420 can have a geometry that limits directional variation, such as a cup seal. Lubricants or other low friction elements can be added. The seal may be compliant or substantially non-compliant.

FIG. 13A, FIG. 13B and FIG. 13c show cross sections of a tube wall 401. FIG. 13A illustrates that a tube 402 can have a constant or varying wall thicknesses 46 along the length of the tube 402. A wall first diameter thickness 46a can be substantially equal to a wall second diameter section thickness 46c and the wall taper thickness 46b.

FIG. 13B illustrates that the wall second diameter section thickness 46c can be substantially greater than the wall first diameter thickness 46a. The wall taper thickness 46b can be less than the wall second diameter section thickness 46c and greater than the wall first diameter thickness 46a.

FIG. 13C illustrates that the wall second diameter section thickness 46c can be substantially less than the wall first diameter thickness 46a. The wall taper thickness 46b can be greater than the wall second diameter section thickness 46c and less than the wall first diameter thickness 46a.

Figure 14B:
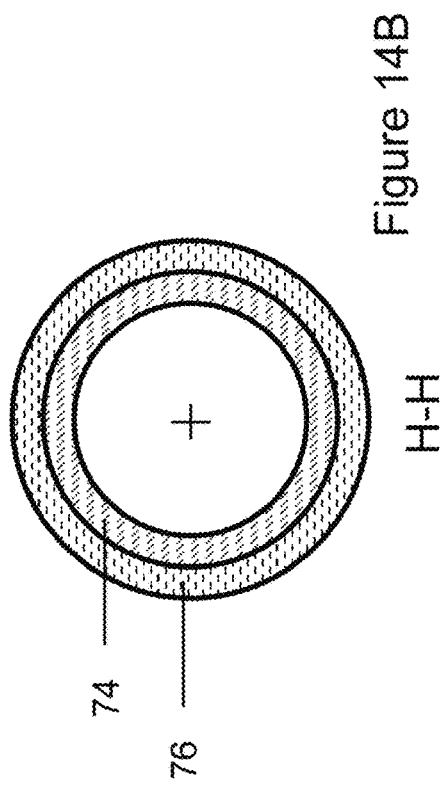
FIG. 14B illustrates a variation of cross section H-H.
Figure 14C:
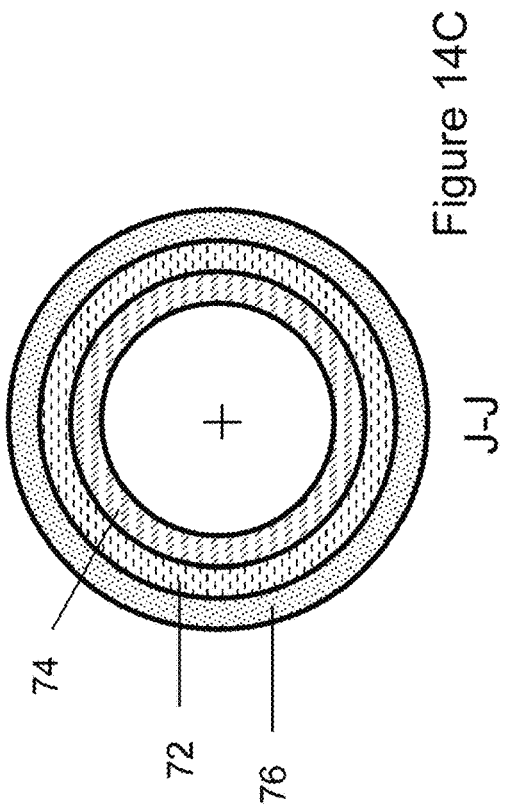
FIG. 14C illustrates a variation of cross section J-J.
Figure 14A:
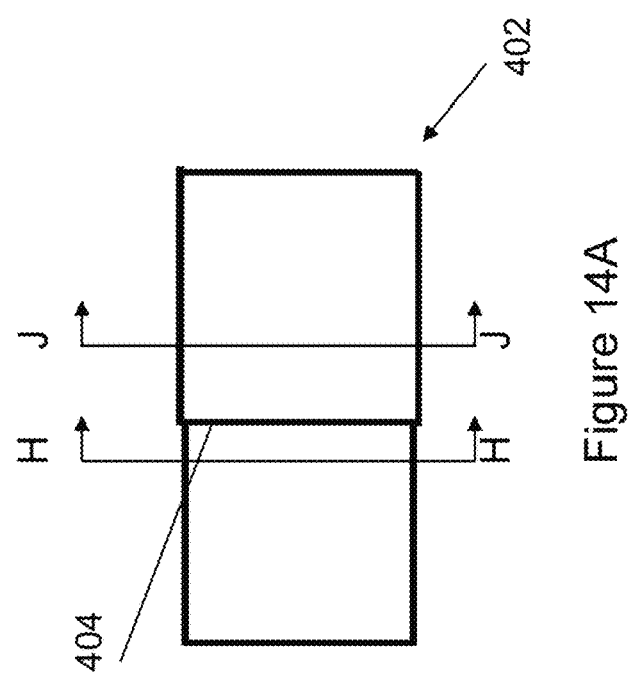
FIG. 14A illustrates a variation of the device.

FIG. 14A shows a tube 402 with seam 404.

FIG. 14B shows a cross section taken at H-H. Wall 401 may contain inner layer 74 and outer layer 76.

FIG. 14C shows a cross section taken at J-J. Wall 401 may contain inner layer 74, layer 72 and outer layer 76.

Any of the layers 72 can be a laminate of fiber and resin. Any of the layers 72 can be a polymer film. Layers may continue across the seam 401 or end at the seam 401. Any combination of the layers can be leak-proof, reinforced with one or more fibers, resistant and releasable from MMA, or combinations thereof. For example, the first layer can be leak-proof and form the bladder. The second layer can be reinforced with a fiber. The third layer can be MMA-resistant and/or MMA-releasing.

Figure 15A:
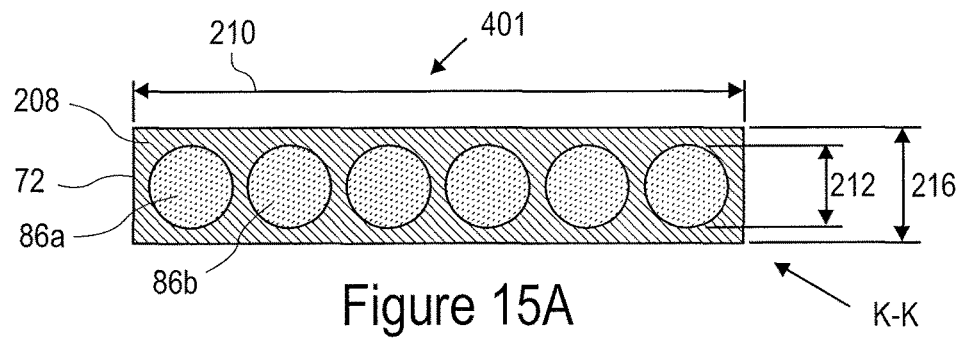
FIGS. 15A through 15O are sectional views through variations of cross section K-K of FIG. 1.

FIG. 15A illustrates that the balloon wall 401 at section K-K or at other sections taken through a single wall of the balloon can have a layer 72 that can have a fiber tape matrix. The fiber tape matrix can have one or more reinforcement fibers 86 and one or more resins. The resin can be a flexible adhesive 208. The flexible adhesive can remain flexible when cured or melted to form the sheath 400.

The fiber tape (also referred to as unidirectional fiber reinforced tape, unidirectional tape, and uni-tape) may have one, two or more monofilaments 86 running substantially parallel to each other and embedded in a flexible adhesive 208. Uni-tape may be produced with a removable backing. The removable backing can be made of paper, plastic, film, metal, elastomer, foam, fabric or combinations thereof. The substantially parallel monofilaments may be positioned within the flexible adhesive such that they are touching each other along their length. The substantially parallel monofilaments may be positioned such that there is flexible adhesive separating each fiber along its length.

FIG. 15A illustrates fiber array layer 72 having a layer width 210 in cross-section. The layer width 210 can include a number of fibers 86, for instance first fiber 86a and second fiber 86b. The layer 72 can have a linear quantity fiber density measured, for example, as the number of fibers 86 per unit of layer width 210. The linear quantity fiber density can be equal to or greater than about 500 fibers per inch, more narrowly equal to or greater than about 1000 fibers per inch, more narrowly equal to or greater than about 2000 fibers per inch, yet more narrowly equal to or greater than about 4000 fibers per inch. For example, the liner quantity fiber density can be from about 1,000 fibers per inch to about 2,000 fibers per inch.

The fibers 86 or monofilaments can be high strength and inelastic. The fibers can have a fiber or monofilament diameter 212, for example, from about 1 μm to about 50 μm, for example less than about 25 μm, more narrowly less than about 15 μm. The unidirectional fiber-reinforced tape can have the same or different sizes and materials of fibers within the same unidirectional fiber-reinforced tape.

The fiber tape layer 72 can have a layer thickness 216 from about 1 μm to about 50 u μm, more narrowly from about 8 μm to about 25 μm, yet more narrowly from about 10 μm to about 20 μm.

Figure 15B:
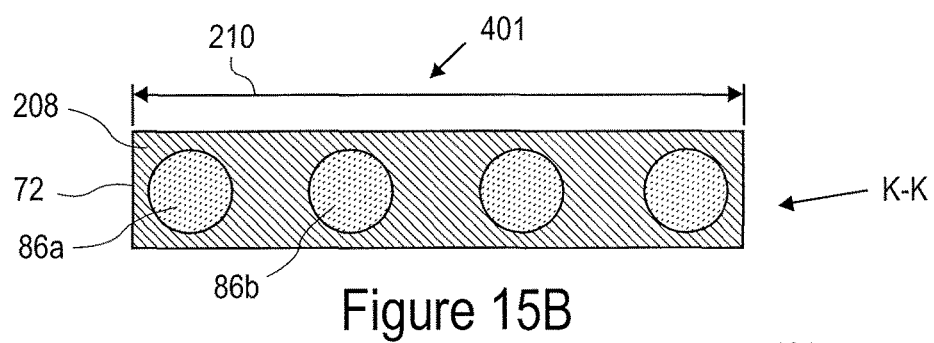

FIG. 15B illustrates that the fiber density can be less than the fiber density shown in FIG. 15A. For example, the fiber density can be about 500 fibers per inch.

Figure 15C:
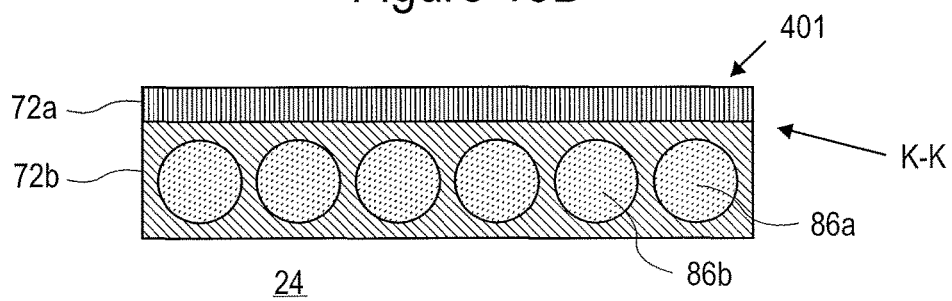

FIG. 15C illustrates that the inner layer 72b can have a fiber tape having reinforcement fibers 86 in an adhesive 208. The outer layer 72a can have a polymer film. The laminate shown can be a part of or the entire wall 401. The internal volume of the sheath volume 24 can be on the radial inside of the sheath.

Figure 15D:
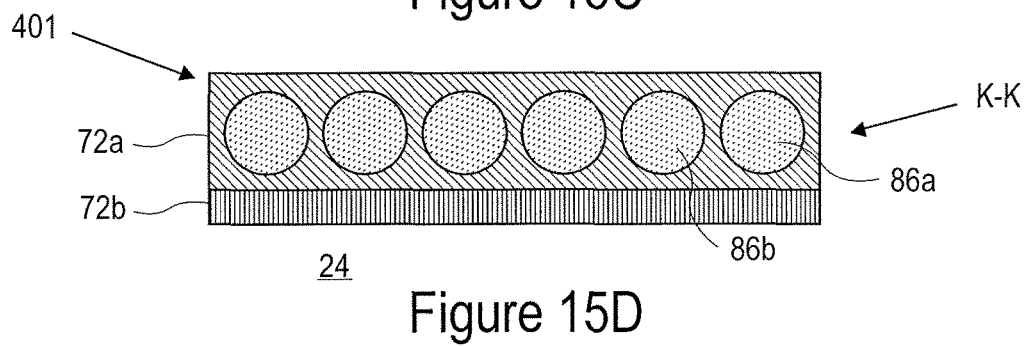

FIG. 15D illustrates that the outer layer 72a can be a fiber tape. The inner layer 72b can be a polymer film.

Figure 15E:
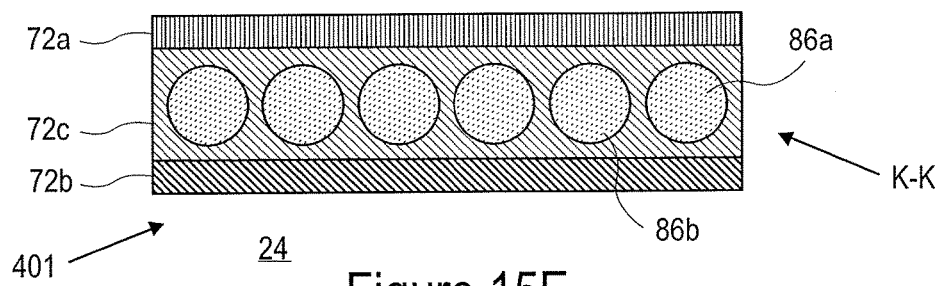

FIG. 15E illustrates that the outer layer 72a and the inner layer 72b can be polymer films. In any variation, the polymer films can be the same or different polymers, or any combination thereof. The first middle layer 72c can be a fiber tape.

Figure 15F:
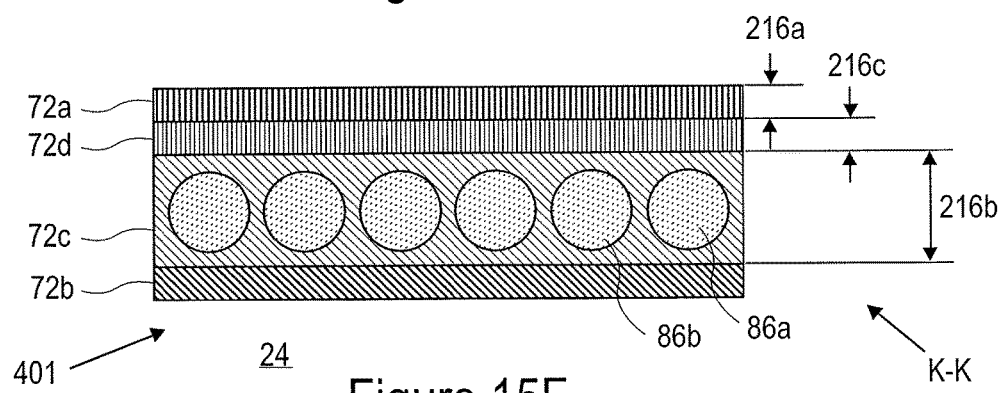

FIG. 15F illustrates that the outer layer 72a, inner layer 72b, and second middle layer 72d can be polymer films. The first middle layer 72c can be a fiber tape. Any adjacent layers, such as the third middle layer 72e and the outer layer 72a can be joined with adhesive, by melting, solvation, welding or combinations thereof.

Figure 15G:
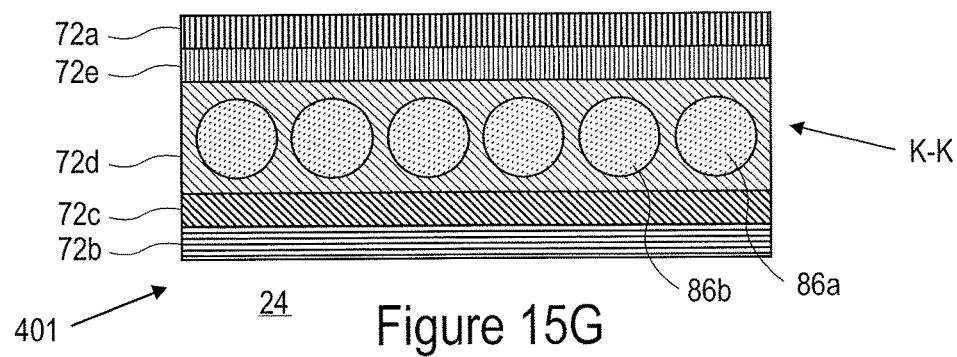

FIG. 15G illustrates the outer layer 72a, inner layer 72b, first middle layer 72c and third middle layer 72e can be polymer films. The second middle layer 72d can be a fiber tape.

Figure 15H:
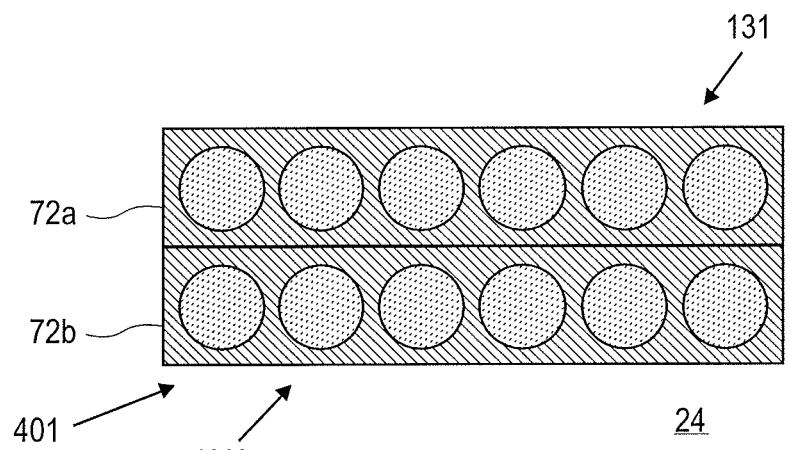

FIG. 15H illustrates that the outer layer 72a can be a first fiber tape. The inner layer 72b can be adjacent to the outer layer 72a. The inner layer 72b can be a second fiber tape. The first and second fiber tapes can be uni-tapes. The fiber in first fiber tape can form an angle with the fiber in the second fiber tape. Part or all of the wall 401 can have multiple fiber tape layers in a wall section area 131. The area 131 can include a number of fibers.

Part or all of the wall 401 can have a volumetric quantitative density of fibers measured, for example, as the number of fibers per unit of area. The area quantity fiber density can be equal to or greater than about 100,000 fibers per square inch, more narrowly equal to or greater than about 250,000 fibers per square inch, more narrowly equal to or greater than about 1,000,000 fibers per square inch, yet more narrowly equal to or greater than about 4,000,000 fibers per square inch. The area quantity of fiber can be about 25% of the area of a wall cross section, more narrowly about 50%, more narrowly about 75%.

The ratio of the volume of the fiber tape to the volume of the fibers 86 can be about equal to or greater than about 15%, more narrowly equal to or greater than about 30%, more narrowly equal to or greater than about 50%, yet more narrowly equal to or greater than about 75%.

Figure 15I:
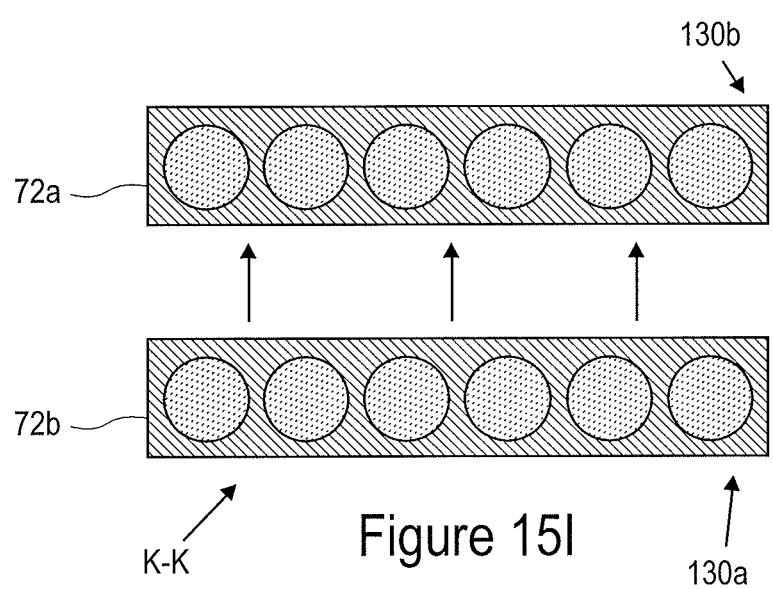

FIG. 15I illustrates that a wall 401 can be made by positioning, as shown by arrows, an inner layer 72b having a first laminate 130a on the outer layer 72a having a second laminate 130b. The first laminate 130a can be consolidated to the second laminate 130b. Consolidation can include heating, pressurizing, solvating, or combinations thereof of the first laminate 130a and the second laminate 130b.

Figure 15J:
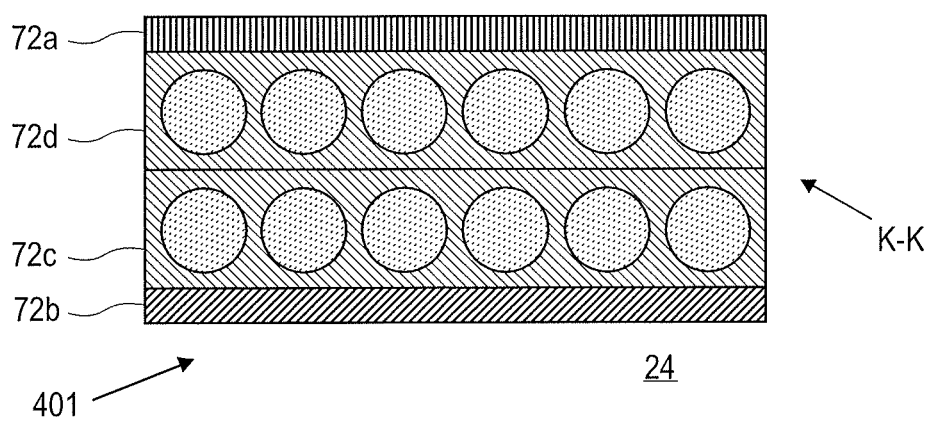

FIG. 15J illustrates that the outer layer 72a, and inner layer 72b can be polymer films. The first middle layer 72c and the second middle layer 72d can be fiber tapes.

Figure 15K:
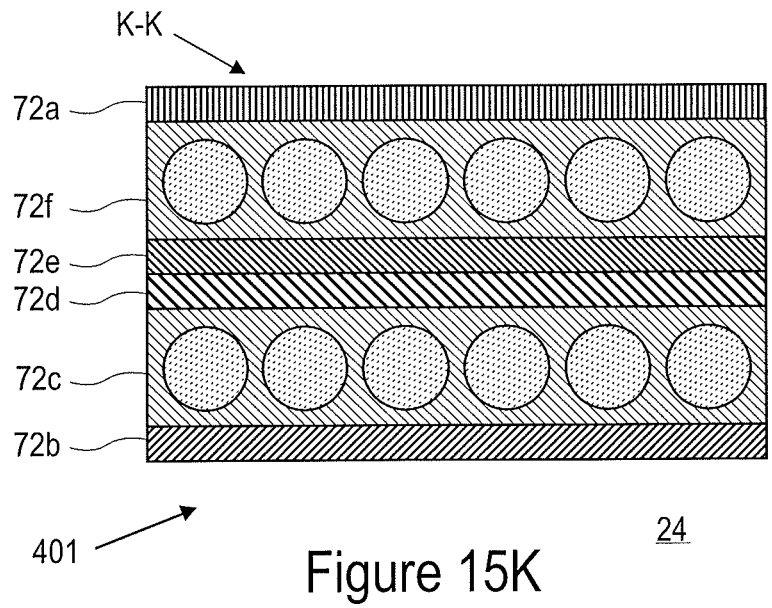

FIG. 15K illustrates that the outer layer 72a, inner layer 72b, second middle layer 72d, and third middle layer 72e can be polymer films. The first middle layer 72c and the fourth middle layer 72f can be fiber tape.

Figure 15L:
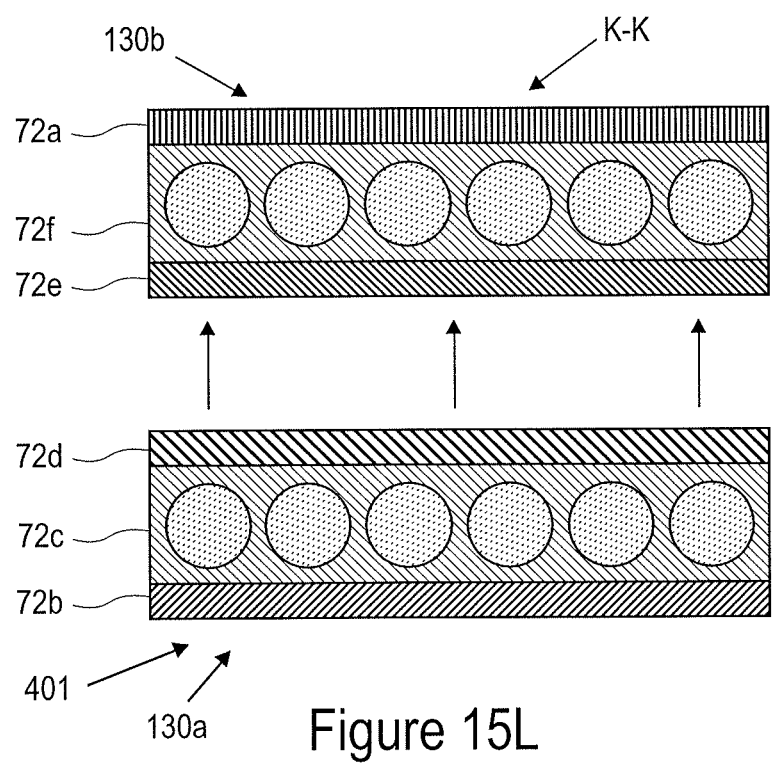

FIG. 15L illustrates that the wall 401 can be made by positioning, as shown by arrows, a first laminate 130a on a second laminate 130b. The first laminate 130a can be consolidated to the second laminate 130b. The first laminate 130a can have the outer layer fixed to the fourth middle layer, which can be fixed to the third middle layer. The second laminate 130b can have the inner layer fixed to the first middle layer, which can be fixed to the second middle layer.

Figure 15M:
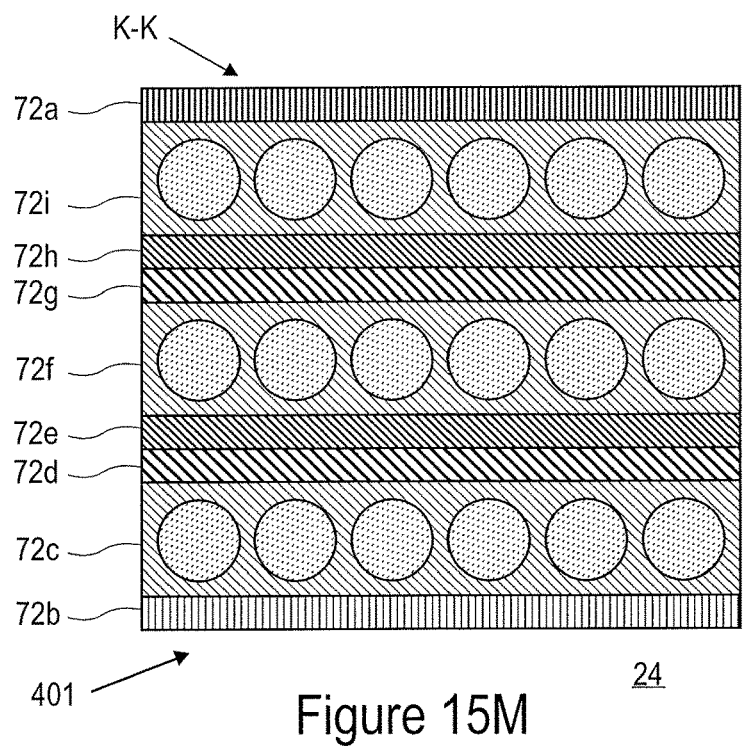

FIG. 15M illustrates that the outer layer 72a, inner layer 72b, second middle layer 72d, third middle layer 72e, fifth middle layer 72g, and sixth middle layer 72h can be polymer films. The first middle layer 72c, fourth middle layer 72f and seventh middle layer 72i can be fiber tapes.

Figure 15N:
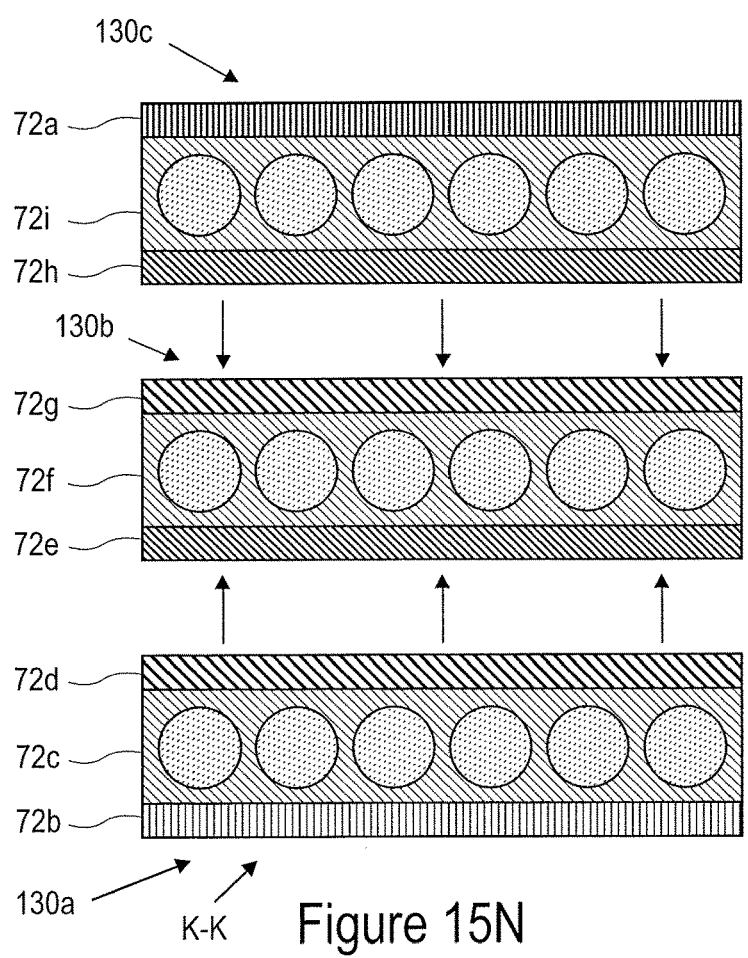

FIG. 15N illustrates that the wall 401 can be made by joining, as shown by arrows, a first laminate 130a, a second laminate 130b, and a third laminate 130c.

Figure 15O:
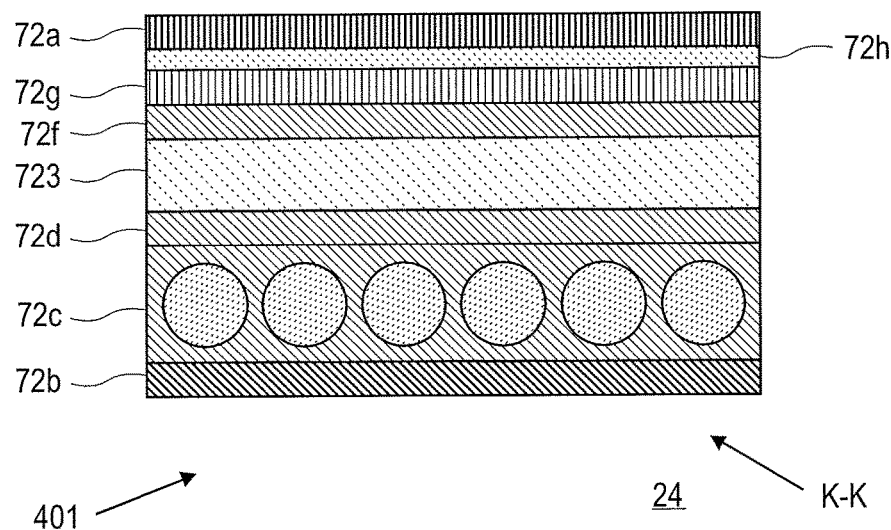

FIG. 15O illustrates that the outer layer 72a can be an MMA-resistant and MMA-releasing polymer film. The inner layer 72b can be a leak proof bladder made from a polymer film. The first middle layer 72c can be a fiber tape, for example with the fibers oriented as longitudinal fibers.

The second middle layer 72d can be a resin or adhesive. The third middle layer 72e can be a fiber tape, for example with the fibers oriented as latitudinal or hoop fibers. The fourth middle layer 72f can be a resin or adhesive. The fifth middle layer 72g can be a radiopaque layer, such as a metal foil or a radiopaque metal foil. The sixth middle layer 72h can be a resin or adhesive.

The radiopaque metal foil and any other radiopaque or metal element herein can be made from gold, platinum, platinum-iridium alloy, tantalum, palladium, bismuth, barium, tungsten, or combinations thereof. Any of the layers can have particles of gold, platinum, platinum-iridium alloy, tantalum, palladium, bismuth, barium, tungsten or combinations thereof. Any of the layers can have radiopaque dyes.

The foil can be less than about 30 µm thick, for example less than about 20 µm thick, for example about 15 µm, about 12 µm, about 10 µm or about 8 µm thick. Radiopaque foils can be cut or patterned by laser cutting, wire EDM, die cutting or deposition. The foils may be mounted to a removable backing before cutting such that a pattern of foils may be easily applied during the balloon construction process.

The panel, such as a foil, can be located in the wall 401 in an area that is exposed to increased stresses during inflation. A radiopaque foil can strengthen the wall 401.

A metal film or foil layer on the outside of the balloon can also be used to resist chemical attack. This metal film or foil layer may give the balloon radiopacity. The outer surface of the balloon may also have a coating that may help the balloon resist chemical attack. The coating may be flouropolymer based.

Any of the polymer or fiber tape layers can be leak proof, water tight, air tight, MMA-resistant, MMA-releasing, or combinations thereof.

Several laminates, each with different fiber orientations and a different number of layers, may be created. Alternately, a single laminate may be constructed with multiple fiber orientations and layer quantities placed into different regions of the larger laminate. From this single laminate, smaller laminates with specific fiber orientations can then be removed and used to create part or all of a tube.

If it is desired that the outside of the laminate be low friction and resistant to harm from chemicals, or that the laminate readily release from certain adhesives (such as, for instance, Methyl methacrylate, a principal ingredient in bone cement), a fluoropolymer such as FEP (Fluorinated ethylene propylene) may be selected for the outer layer. One side of the FEP film can be treated via a plasma method or any other method for allowing routine adhesive bonds to fluoropolymers. The treated layer can face into the adhesive matrix, such that it can form a strong bond, while the outer layer faces out and provides the desired chemical and mechanical properties The materials that form a laminate may be modified by the addition of certain elements that give desired additional properties useful for tube wall 401 and tube 402.

Radiopacity may be a desired property in a sheath. Radiopacity may make the sheath visible to the medical practitioner during a procedure. For instance, the radiopaque materials may cause the sheath to be visible with a fluoroscope.

Radiopaque materials may be added to the adhesive, the fiber or the film used to create a laminate.

Radiopaque materials may be added to the adhesive that is used to create a fiber tape. For instance, particulate could be added to the adhesive. This particulate could be made out of aluminum, titanium, lead, tungsten, bisumuth, tantalum or combinations thereof, for example US Aluminum Power, Part Nos. US254012 or US15212. The particulate can be added to the adhesive with a homogenizer, an ultrasonic mixer, by using shear dispersion, by using hydraulic dispersion or by other mixing technologies.

Radiopacity could also be added by mixing typical radiopaque dyes into the adhesive. The added materials could mix with the adhesive or be dissolved in it.

The added material may co-react with the adhesive. For instance, the material may end up cross-linked with the base adhesive.

Radiopacity could also be added to the laminate by embedding materials in the polymer film of the laminate. During the formation of the polymer film, materials such as those mentioned above could be dispersed, mixed, dissolved or cross-linked with the film.

A polymer film that is made part of a laminate could also be coated with one or more materials, such as a metal, that would give the film radiopacity. A coating could be vapor deposited, sputter coated, solution coated, reverse roll coated, slot dye coated, air dye coated, gravure coated, spray coated, electrostaticly coated, ink jet printed or coated in some other way known in the art. The purpose of applying this film may also be to give the tube electrical conductivity for some clinical purpose.

The polymer film may also be printed with an antennae pattern of some kind. This would allow the tube to selectively absorb RF radiation. The RF radiation could be used to drive a load in or on the tube, such as a heater or other device. The heater could be built out of carbon fiber with resistivity fabricated such that it acts as a heating element for the current produced by the antennae.

The fibers in the fiber tape may also serve to give the resulting laminate radiopacity to X-rays. The fibers could be coated, using the same methods as described for films. Particulate, dyes or other materials can be added during the formation of the fibers such that they have significant radiopacity.

Magnetic resonance visualization enhancement materials, such as magnetic contrast agents, can be added to the adhesive, the film or the fiber. The magnetic resonance visualization enhancement materials can enhance the visualization of the balloon during an magnetic resonance imaging (MRI) procedure. For example, the magnetic resonance visualization enhancement material can be gadolium, Omniscan, Optimark, ProHance, Magnevist, Multihance, or combinations thereof.

Any of the layers, for example the outer layer, can be tinted or dyed a visible spectrum color. For example, a pigment, coloring additive, dispersions or other coloring agents, such as an coloring additive from Plasticolors (Ashtabula, Ohio) can be added to the adhesive, laminate or fiber before consolidation. A paint or coating can be added to a layer surface or to the outer surface of the balloon wall.

The color can be selected for branding, market differentiating, as an indication of the type of device, the size of the device, or combinations thereof. For example, devices having a selected diameter, length, pressure rating, clinical indication or efficacy, other common performance metric, or combinations thereof, can be dyed a specific color (e.g., green for a first type of device, red for a second type of device).

The layers can have one or more optical fibers. The fiber optic can be a strain sensor. The strain sensor can monitoring the laminate's mechanical status in real time. The fiber optic can guide light delivery into the body. The fiber optic can visualize a target site (e.g., gather light from the body to produce a visual image).

A strain gauge could also be added to the laminate during manufacture. This strain gauge could allow real time monitoring of the laminate mechanical status. The laminate could be used in the body as part of a larger structure such as a tube, or the laminate could be used by itself.

Reducing the transport of gas or liquid thru the laminate may be a goal of these additives. For example, Angstrom Materials's (Dayton, Ohio) nano-scaled grapheme platelet raw materials can be added to the adhesive. Other nanomaterials may be added to the adhesive, film or fiber to improve such properties as adhesion, strength or stiffness.

The design of the laminates may give the laminate high strength or high toughness or high flexibility or resistance to abrasion or resistance to tearing (i.e., rip-stop) or resistance to extreme temperatures or resistance to dielectric breakdown or resistance to chemicals or for combinations thereof or any other property that may be incidental to the materials or construction and is appropriate to the application or for combinations thereof.

FIG. 16 illustrates polymer films from which the layers can be made. The thickness of the polymer films can be from about 2 μm to about 50 μm, more narrowly from about 2 μm to about 18 μm, yet more narrowly from about 4 μm to about 12 μm. These films may be chosen for their high strength or high toughness or resistance to abrasion or resistance to extreme temperatures or resistance to dielectric breakdown or resistance to chemicals or for combinations thereof or for any other property that they naturally have that is appropriate to the application or for combinations thereof.

FIG. 17 illustrates materials from which the reinforcement fibers can be made.

FIG. 18 illustrates that the adhesive can be an elastomeric thermoset material, an elastomeric thermoplastic material, or a combination thereof. The adhesive can be selected from any of the materials, or combinations thereof, listed in FIG. 18. The matrix can have a resin and a fiber. The resin can be an adhesive.

Method of Making

Figure 19:
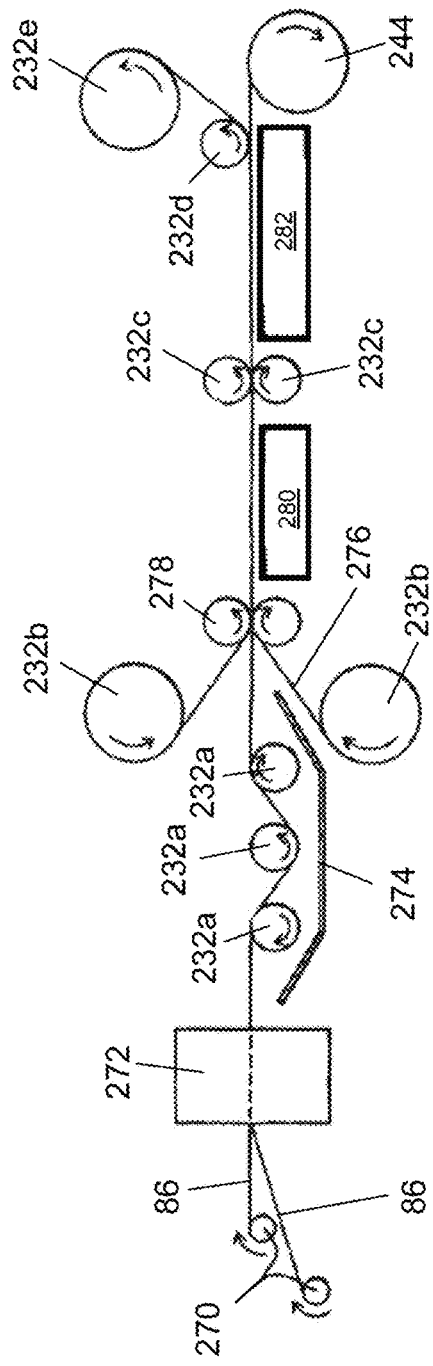
FIG. 19 illustrates a portion of a method that may be used to produce unidirectional fiber tape.
Figure 20:
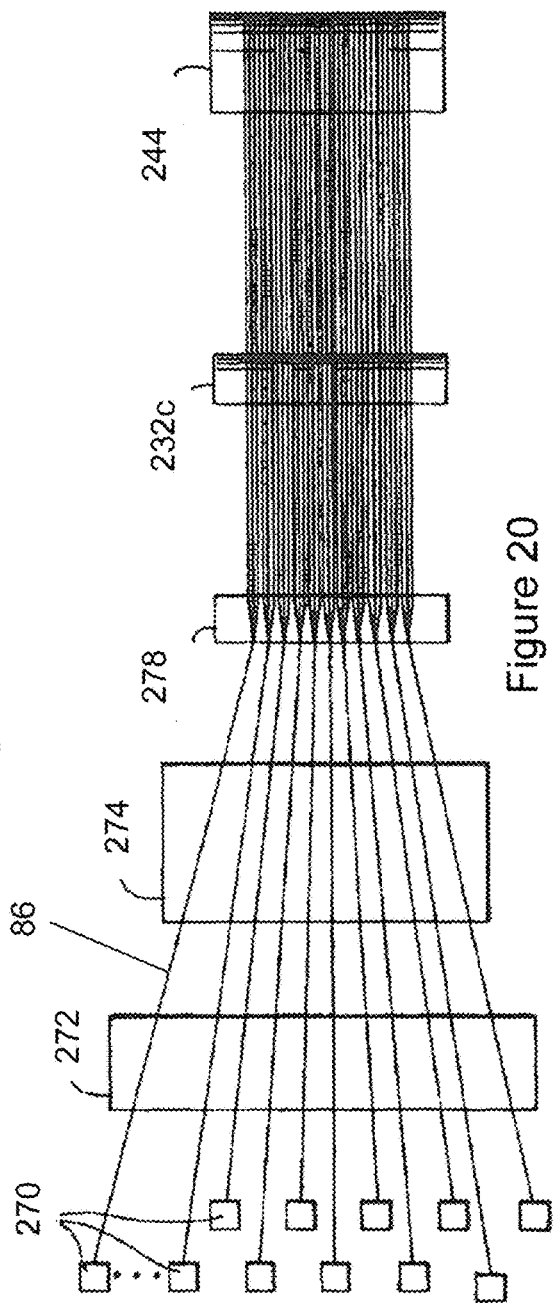
FIG. 20 illustrates a portion of a method that may be used to produce unidirectional fiber tape.

FIG. 19 and FIG. 20 illustrate one method of uni-tape fabrication. Tows or bands 270 provide the extruded monofilaments or fibers 86 which are optionally passed through a treatment bath 272 to improve adhesive bonding features of the exterior of the monofilaments via chemical etching, plasma arc etching or corona discharge etching. The pretreated monofilaments from the tows are pulled through an adhesive bath 274 over and under first rollers 232a where the matrix adhesive coats and surrounds the monofilaments.

The adhesive-coated monofilaments are drawn through a fixed gap rotary die 278. Release material 276 from second rollers 232b can be applied to the top and bottom of the adhesive coated monofilaments, for example, prior to the pulling of the tows 270 through the fixed gap rotary die 278 which controls adhesive content and spreads the filaments. During a pull-trusion process, the individual tows are laterally joined to form a uni-tape which is heated by a heater 280 for viscosity change, after which the tape is compacted via rolls third rollers 232c. The compacted tape can then be passed over a chill plate 282 to the spool 244, with the top sheet of release material being removed at roll fourth roller 232d and reeled up on fifth roller 232e.

The monofilaments can be subject to less than about 0.02 pounds of tension during assembly substantially immediately before the monofilaments set in the adhesive matrix. For example, substantially no tensioning can be applied to the monofilaments during manufacturing immediately before the monofilaments set in the adhesive matrix.

Another kind of fiber tape (hereafter referred to as woven tape) may have a woven, knitted or braided fiber cloth, a flexible adhesive, and an optional removable backing or combinations thereof. The removable backing can be made of paper, plastic, film, metal, elastomer, foam, fabric or combinations thereof.

Woven, knitted and braided cloths are known though modern textile products. Typically, weave patterns feature a warp threads, running in a first direction, and weft threads, running in a second direction. The angle between the first and second directions may be 90 degrees. The angle between the first and second directions may be 75 degrees. The angle between the first and second directions may be 60 degrees. The angle between the first and second directions may be 45 degrees. The angle between the first and second directions may be oriented at any appropriate angle. In the process of weaving, the threads may be interlaced in various ways to form weave patterns depending on the properties desired.

Another kind of fiber tape (hereafter referred to as matted tape) can have matted fiber, a flexible adhesive, and an optional removable backing or combinations thereof. The removable backing can be made of paper, plastic, film, metal, elastomer, foam, fabric or combinations thereof. The matted fiber may be a collection of randomly oriented fibers of different lengths.

Figure 21:
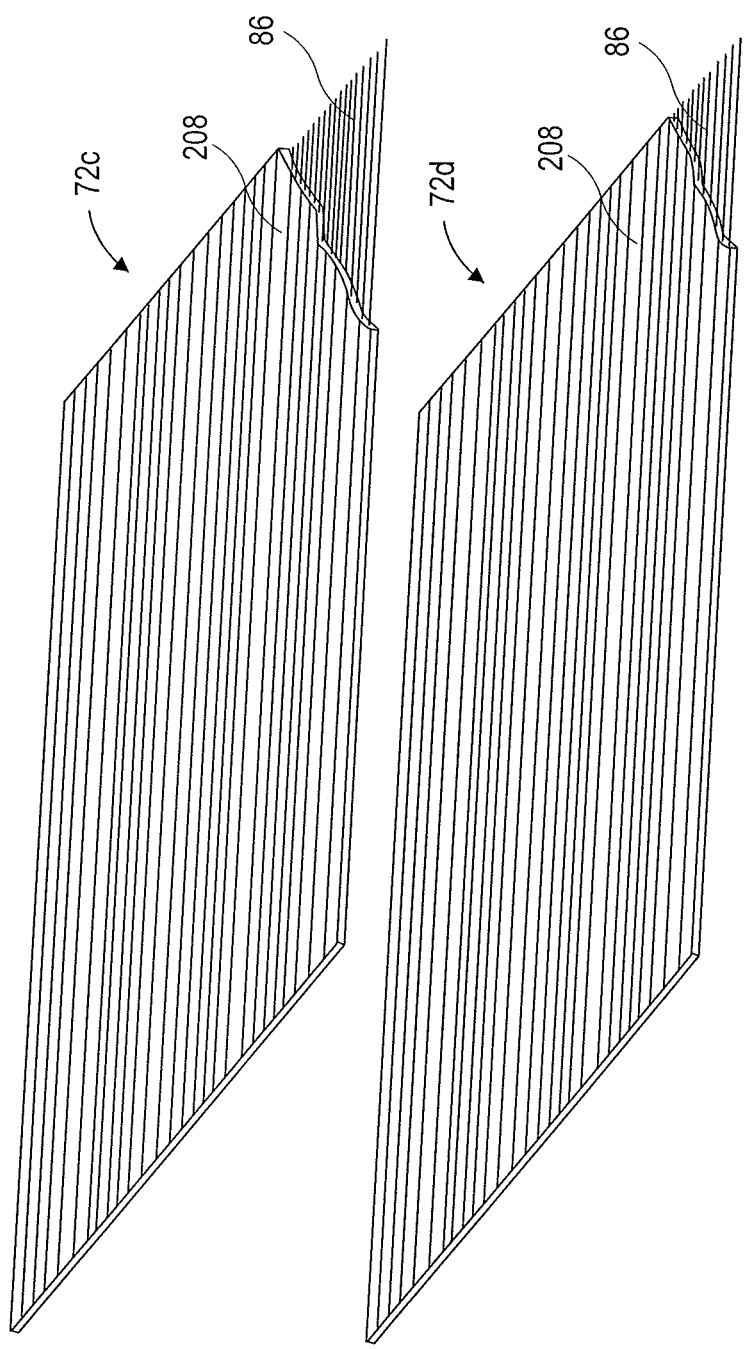
FIGS. 21 through 24 illustrate variations of arrangements of unidirectional fiber tape.

FIG. 21 shows that layers 72c and 72d can have reinforcement fibers 86 oriented in the same direction. This is a 0-0 arrangement, because of the angle that each layer 72d makes with a vector aligned with the fibers of the bottom layer 72c. This arrangement may provide twice the strength in the fiber direction as the uni-directional tape itself.

Figure 22:
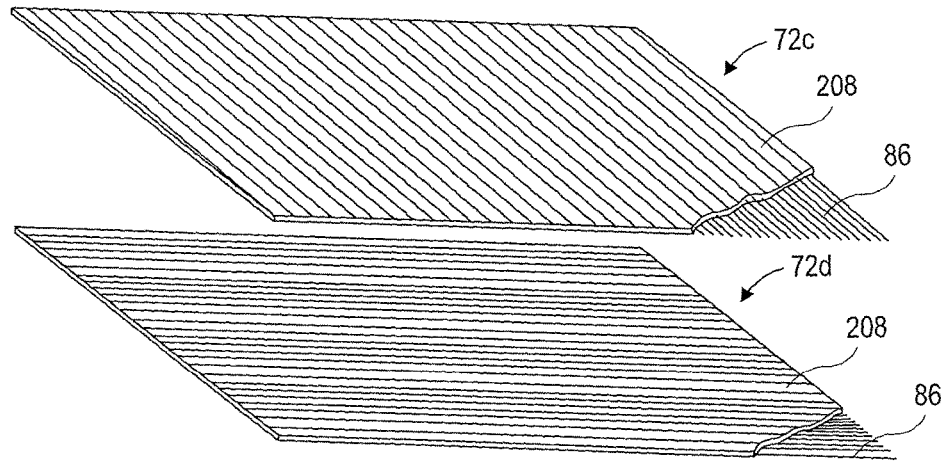

FIG. 22 shows that layers 72c and 72d can have reinforcement fibers 86 oriented perpendicular to each other. This is a 0-90 arrangement, because of the angle that the second layer 72d makes with a vector aligned with the fibers of the bottom layer 72c. This arrangement may provide substantially the same strength in the 0 degree and 90 degree direction as the uni-directional tape itself.

Figure 23:
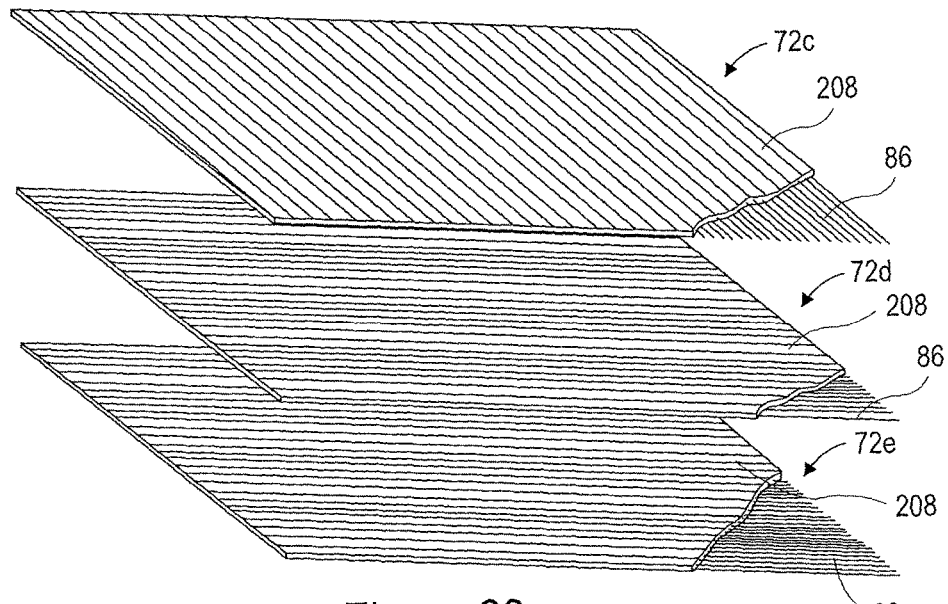

FIG. 23 shows that layers 72c, 72d and 72e can have reinforcement fibers 86 oriented at 0-0-90 to each other. This arrangement may provide approximately twice the strength in the 0 direction than a single layer of uni-tape provides. This arrangement may provide strength in the 90 direction approximately equal to that of a single uni-tape.

Figure 24:
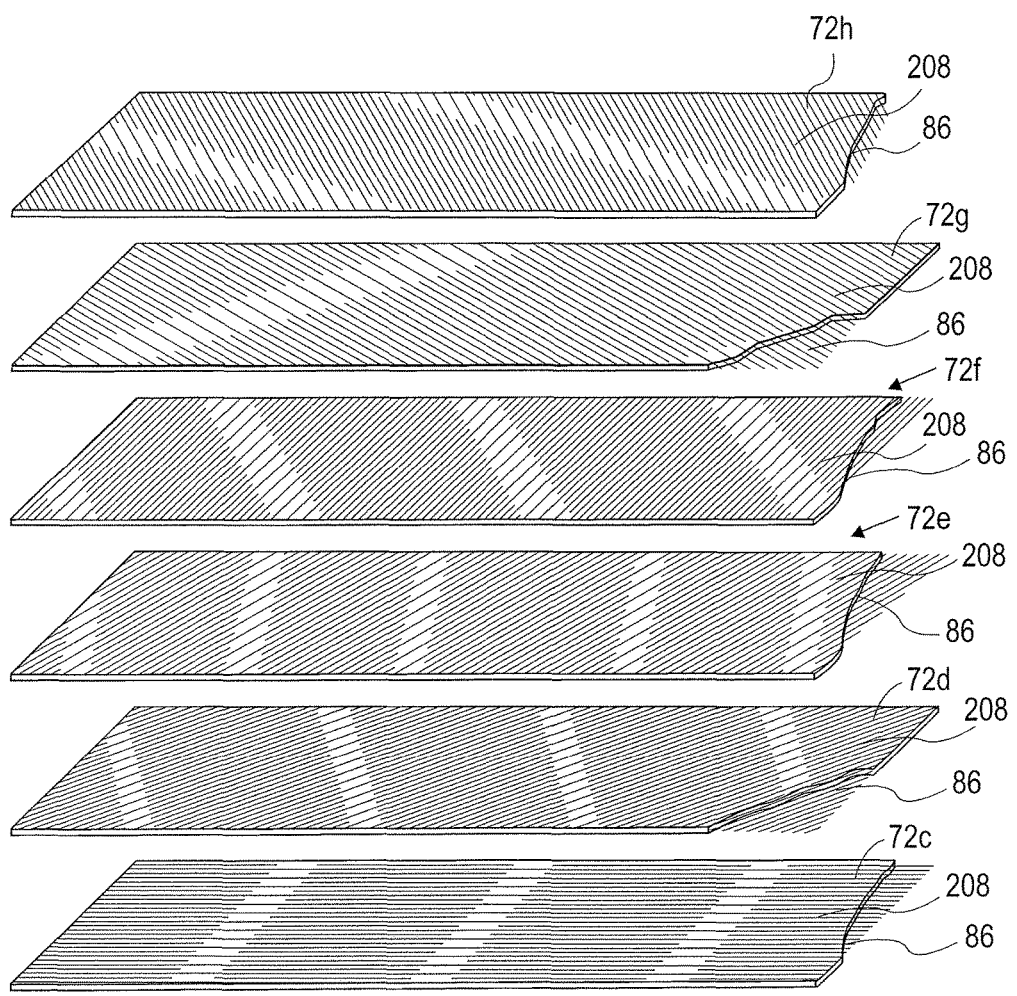

FIG. 24 shows that layers 72c, 72d, 72e, 72f, 72g, and 72h can be oriented at 0, 30, 60, 90, −30, −60 respectively to each other.

A laminate may include one or more fiber tapes. A laminate may include one or more polymer films.

The one or more fiber tapes and, optionally, the one or more polymer films can be consolidated into a laminate. Consolidation may include compaction and curing or melting. Compaction can occur before curing or melting. Compaction may include the application of heat and/or light and/or an electron beam, the application of force (i.e., pressure), and the passage of time. Curing or melting may include the application of heat or light, the application of force (i.e., pressure), and the passage of time.

During the process of consolidation, fibers may shift position within the laminate. During the process of consolidation, the fibers may get closer to each other within the laminate.

The polymer film or polymer films may melt during the consolidation process or the polymer films may not melt. The polymer films can be on one or both outer surfaces of the laminate and different materials can be put on each side. The polymer film can be on only one side of the laminate, or absent altogether.

The polymer film could be formed by applying a polymer in a wet application process, such as spraying, dipping, painting, or combinations thereof.

The polymer film may be coated with a material. The coating may be applied by, for instance, sputter coating. The material that is coated on the polymer film may provide substantial radiopacity.

Figure 25:
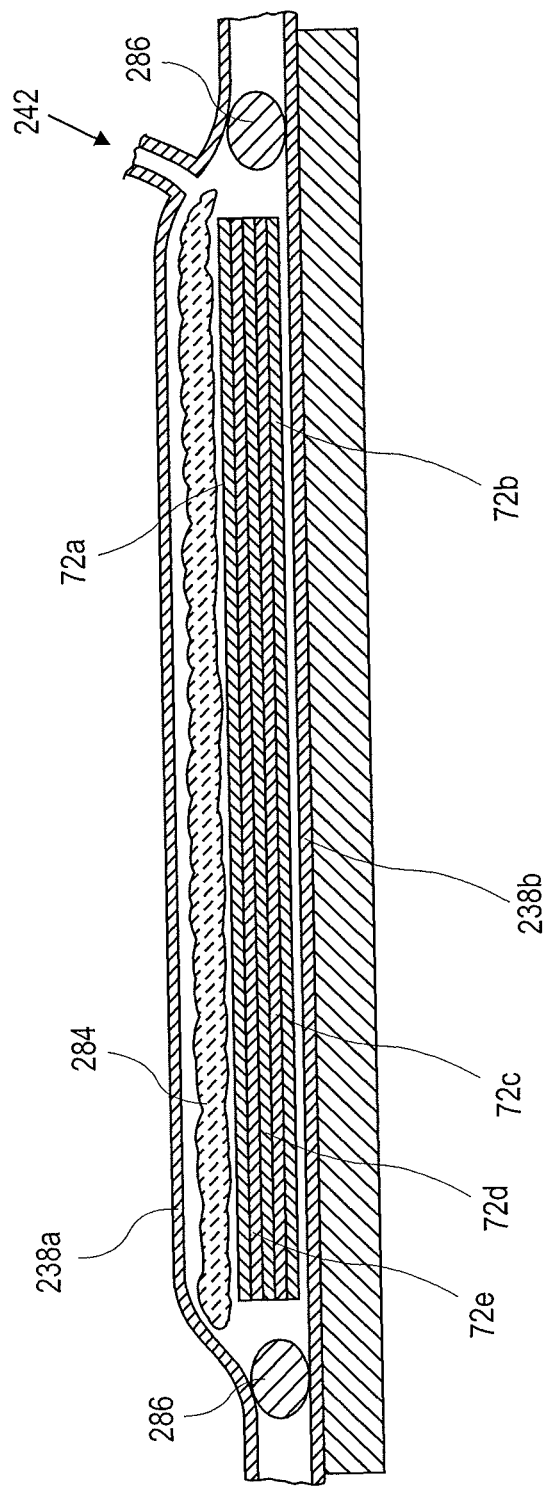
FIG. 25 illustrates a variation of a method for making a laminate.

FIG. 25 shows an example of the fabrication of a laminate by using an auto clave. Various layers of fiber tape material 72c, 72d, and 72e can be between an outer layer 72a of a film and an inner layer 72b of a film. The fiber tape material and the films can be between a top vacuum sheet 238a and a bottom vacuum sheet. The bottom vacuum sheet can be placed on a rigid plate or platen 288. Sealing is provided by seals 286. A breather material 284 may be between the outer layer 72a and the top vacuum sheet 238a, for example for evacuating gas from between the vacuum sheets. The enclosed volume or bag between the top and bottom vacuum sheets can be evacuated at the suction tube 242.

Figure 27:
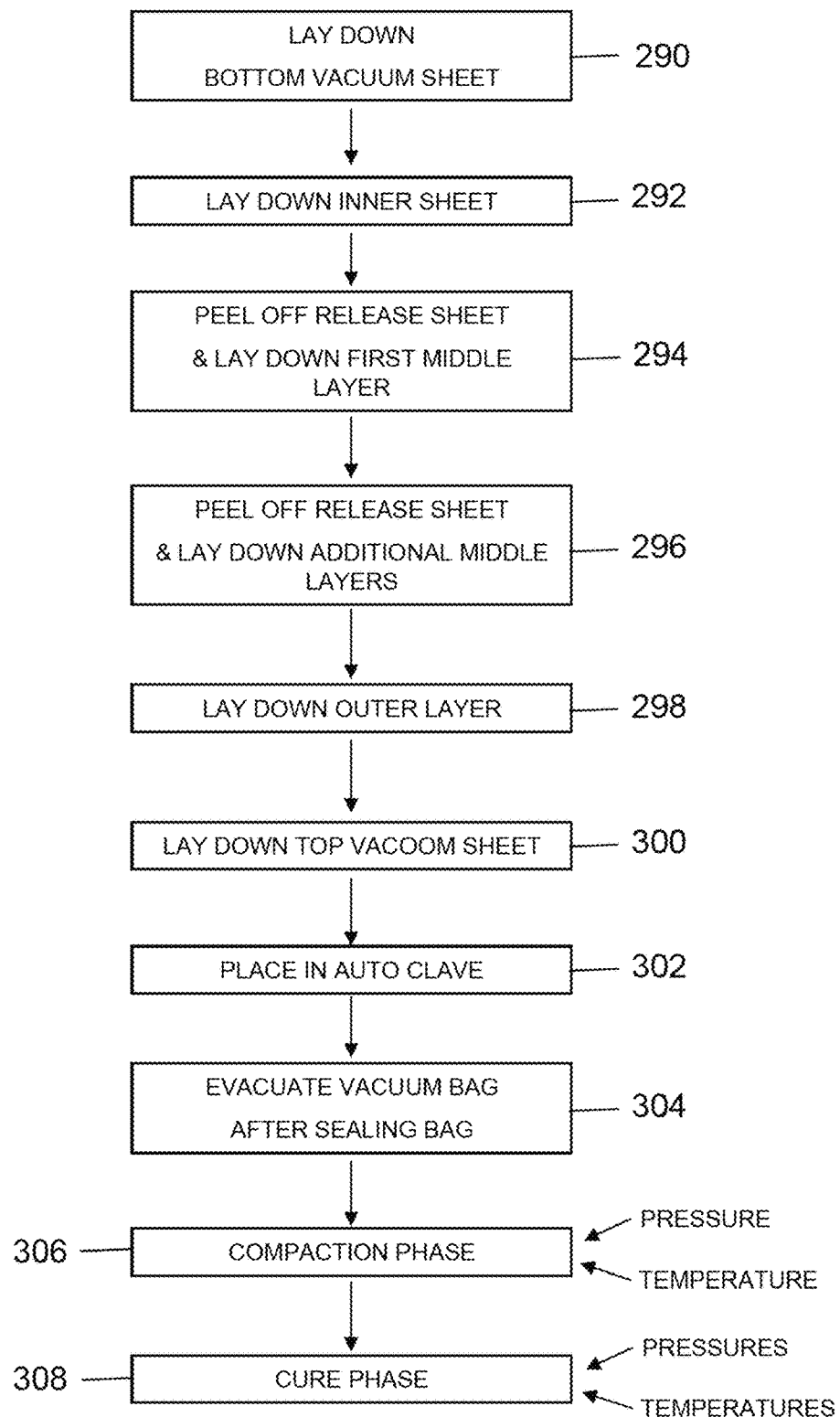
FIG. 27 is a process flow chart of a variation of a process for making a laminate.

During the autoclave process as illustrated in FIG. 27, the process steps are first to lay down the bottom vacuum sheet as illustrated at 290. Secondly, one optionally lays down the inner layer 292 to be laminated or consolidated as illustrated at 292, followed by the peeling off of the removable backing and laying down the first middle layer as illustrated at 294. Thereafter as illustrated at 296, optional additional middle layers can be laid down after removal of their removable backing. Additional fiber tape can be laid down in additional directions as needed. Thereafter, the outer layer can be optionally laid down as illustrated at 298. A breather material 284 may be positioned between the outer layer and the and top vacuum sheet. The top vacuum sheet can be laid down over the breather material 284 as illustrated at 300. The structure can be placed in an autoclave as illustrated at 302. The volume between the bottom and top vacuum sheets can be evacuated after sealing the edges as illustrated at 304.

Thereafter, as part of a consolidation phase, follows a compaction phase as illustrated at 306 at the requisite pressures and temperatures. Thereafter, as part of a consolidation phase, follows a curing or melt phase as illustrated at 308 at associated pressures and temperatures.

Figure 26:
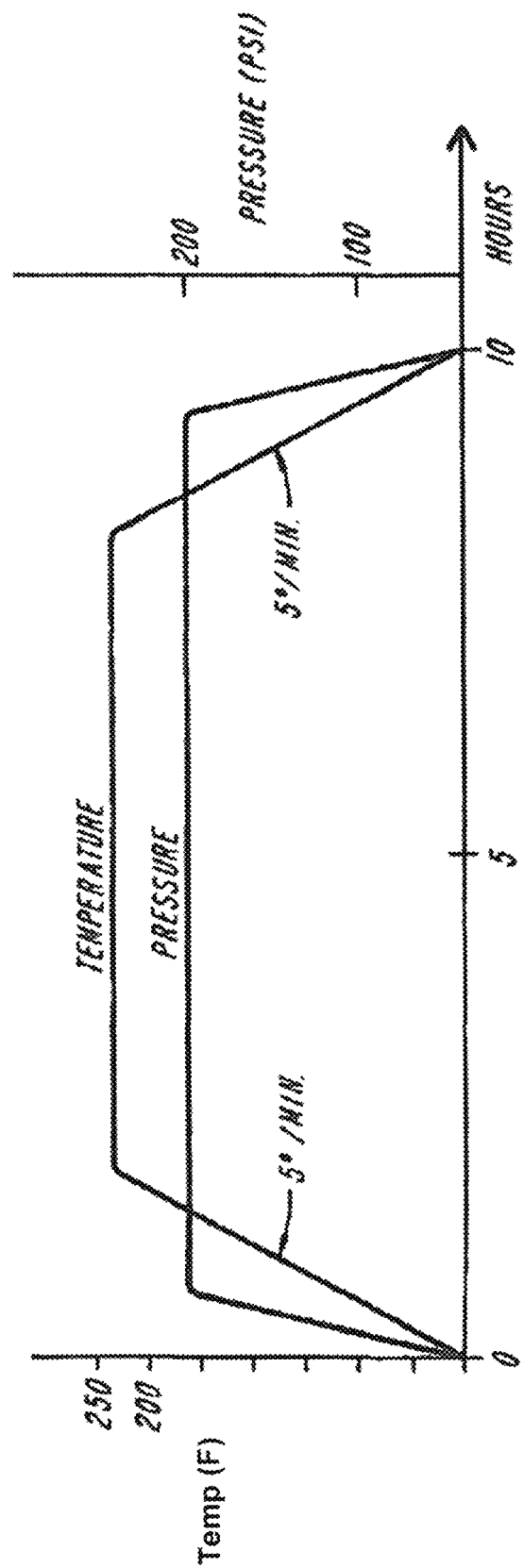
FIG. 26 is a graph illustrating a variation of temperature and pressure versus time graph for a method for compacting or curing or melting that can be used with a fiber tape.

One set of pressures and temperatures useful for a compaction or cure or melt phase is illustrated in FIG. 26 by the temperature time graph and associated temperature pressure graph.

Several laminates, each with different fiber orientations and a different number of layers, may be created. Alternately, a single laminate may be constructed with multiple fiber orientations and layer quantities placed into different regions of the larger laminate. From this single laminate, smaller laminates with specific fiber orientations can then be removed and used to create a medical inflatable.

The laminate can be made as describe in U.S. Pat. No. 5,333,568 or 5,470,632, both of which are herein incorporated by reference in their entireties.

A layer may be leak tight. The layer may be made by dip molding, for example, urethane or nylon, over a mandrel. The layer may be made by rotational molding.

The layer may be made by coating a substance over a mandrel or a layer 72. A coating may be, for instance, parylene. A coating may be a metal, such as gold. A coating may be electrodeposited, electroless deposited or via physical vapor deposition or a combination thereof. A coating may have significant radiopacity. A coating may increase the toughness of the balloon, or increase its lubricity. A coating may reduce or eliminate attack or adhesion from chemicals. For instance, a coating may cause the balloon to not be attacked or to adhere to bone cement.

A layer may be formed by conformal coating. A conformal coating may include a flouropolymer. The coating may be dipped on, sprayed on or applied by electrostatically charging the substrate or by combinations thereof. Coatings may be cured by baking.

A layer may be formed by blow molding. The blow molding process can include a parison. The parison may be open at both ends, or only open at one end (i.e., a blind parison).

FIG. 28A illustrates that a layer of fiber tape can be made on a roller 232. The roller can be configured to rotate about a roller axle 234. The roller may have a diameter from about 100 mm to about 1,000 mm. The roller may be made or coated with an anti-stick material such as a flouropolymer.

FIG. 28B illustrates that a releaser 236, such as a release layer, can be placed around the circumference of the roller 232. The release layer can be a low friction film or coating. The release layer may be a thin/flexible flouropolymer sheet.

FIG. 28C shows that an adhesive layer can be placed on the releaser or directly onto the roller (e.g., if no releaser is used). The adhesive layer may be a thermoplastic film. The adhesive layer may be a thermoset adhesive. The adhesive layer may be a solvated thermoplastic or thermoset.

FIG. 28D shows the application of fiber to the roller. Fiber may be unwound from a spool (not shown) and rolled onto the top surface of the adhesive. The fiber may contain one or more monofilaments. The fiber may have been previously flattened as detailed in this application. Any coating or sizing on the fiber may have been removed using a solvent. The fiber may be placed with a gap between each successive fiber wrap. The gap can be less than about 25 um, more narrowly less than about 5 um.

FIG. 28E shows a reinforcement layer on top of the adhesive on top of the release layer.

FIG. 28F illustrates that the roller can be placed between a vacuum top sheet 238a and a vacuum bottom sheet 238b, for example in a vacuum bag. A vacuum seal tape 240 can surround the roller between the vacuum bottom and top sheets. The air can be removed from between the vacuum top and bottom sheets and within the vacuum seal tape, for example by suction from a suction tube 242. Inside and/or outside of the vacuum bag, the roller can be heated, for example to melt or cure the adhesive.

FIG. 28G shows the removal of the layer. For instance, a cut may be made substantially perpendicular to the fiber. The layer may be peeled away from the release layer.

FIG. 28H illustrates that the layer of fiber tape can be removed from the roller. For example, the layer can be peeled off the releaser.

The layer can be cut into a pattern. For instance, the layer can be cut with the trimming jig, a laser, a water jet cutter, a die cut tool, or a combination thereof.

FIG. 29 illustrates that part or all of the sheath 400 may be constructed by forming one or more layers 72 into the tube wall 401 and/or tube 402. The layer thickness 430 of layer 72 may be from about 0.0005 in. to about 0.020 in.

FIG. 30 illustrates that a first layer 72a may be attached to a second layer 72b with an offset distance 434. First layer 72a may be a fiber reinforced laminate. Second layer 72b may be a polymer film (such as that listed in FIG. 16) covering a portion of the side of the laminate that will end up on the outside of the tube. Second layer 72b may extend beyond the edge of first layer 72a. First layer 72a may be rolled such that layer edge 432a is the first edge rolled and second layer edge 432b is the last edge rolled. This may allow layer 72b to overlap itself on the outside of the resulting tube. Adhesive may be applied in this overlap 438 (shown in FIG. 31) to form an outer layer film layer for the tube.

FIG. 31 shows first layer 72a and second layer 72b as a partially formed tube 436. The layers 72 can be rolled so as to form a small overlapping seam 438. The layers 72 may be rolled around a solid form such as a tubular mandrel (not shown). Adhesive may be placed inside the overlapping seam 438. If the laminate is not consolidated, adhesive in overlapping seam 438 may be omitted.

Referring now to FIGS. 32A and 32B, first layer 72a and second layer 72b may be rolled so that the sheet goes around substantially more than twice to make a partially formed tube 436. Layers 72 may be rolled exactly twice to form a tube 436. Layers 72 may be rolled around three times or substantially more than three times to form a tube 436. Layer 72b may be substantially wider than layer 72a such that, when a tube is formed, layer 72b wraps around about 2 times and layer 72a wraps slightly more than one time.

FIGS. 33A to 33G show a method of making a tube 402. A sheath 400 can be a single tube 402 or multiple tubes 402. FIG. 33A shows an inflatable mandrel 440. The mandrel can be inflated through a closeable inflation port 442. The mandrel 440 may be a thin walled soft structure made out of, for instance, silicon or some other elastomer.

FIG. 33B shows inflatable mandrel 440 with thin walled tube 444 placed over it. Thin walled tube 444 may be one of the materials shown in FIG. 16.

FIG. 33C shows layer 72 being wound over thin walled tube 444 in a spiral fashion. Each spiral may overlap with the previous turn, thus allowing layer 72 to mostly or completely cover thin walled tube 444.

FIG. 33D shows the process after the spiral wind of layer 72 is complete. Optional additional layers may be applied at this point (not shown). An additional layer may be a film.

FIG. 33E shows the inflatable mandrel 440, the thin walled tube 444 and the layer 72 being placed into a cavity mold. The top of the mold 446 is shown aligned with the bottom half of the mold 448.

FIG. 33F shows the top of the mold 446 closed on the bottom of the mold 448 and enclosing the inflatable mandrel 440, the thin walled tube 444 and the layer 72.

In FIG. 33G, internal pressure 450 may be applied to the mandrel 440. The assembly may be placed in an oven, for example and cured at, for instance, 130° C. for two hours. This may cause layer 72 to bond with thin walled tube 444. After this cure cycle, we may deflate and remove mandrel 440 to free sheath 400.

FIG. 34 shows a partially formed tube 436 built over a solid mandrel (not shown). The solid mandrel may be, for instance, a metal bar inside the partially formed sheath 436. The mandrel may be mounted to chuck 454 which has chuck rotation 456. Reinforcement fiber 86 may be fed from spool 244 which has spool rotation 254. By feeding spool 244 lengthwise as chuck 454 rotates, a layer of reinforcement fiber 86 may be applied to partially formed tube 436. Adhesive may be added to the reinforcement fiber. Additional layers may be laid on top of the reinforcement fiber 86.

FIG. 35 illustrates that the partially formed sheath 436 can be placed in a vacuum bag. The vacuum bag may be formed of a top vacuum sheet 238a and a bottom vacuum sheet 238b and vacuum seal tape 240. Air may be removed from the bag via suction tube 242. The interior of the vacuum bag can be heated. The vacuum bag can be inserted inside of an oven or autoclave. The layers of the partially formed sheath 436 on the mandrel can be thermally cured or melted, for example under from about 1 ATM to about 30 ATM of pressure. The bag delivery channel can suction the interior of the vacuum bag. For example the pressure in the vacuum bag can be less than about 0.1 ATM.

A removable mandrel may be used in constructing a tube. The mandrel can be formed of a low melting point wax or metal, a foam, some collapsing structure, an inflatable bladder, a starch, a salt, a sugar, a Polyvinyl Acetate or the like or combinations thereof. The mandrel may receive an optional polymer coating that may form a wall. The wall can be less than about 0.001 in. thick. Laminates may be laid on the mandrel. The laminates may have adhesive applied to them. The mandrel and laminates may be placed in a vacuum bag. The vacuum bag may be placed at a low pressure, for example zero pressure, such that the laminate is compacted. The mandrel and laminates may have a section of heat shrink tubing placed around it. The mandrel and laminates may be consolidated to create a tube. The mandrel may be removed, generally by placing the tube and mandrel at an elevated temperature or by some other way of collapsing the body of the mandrel.

Additional laminates can be added to areas of a tube that might require extra strength for certain procedures or uses. A tube may have different amounts of fiber, adhesive or polymer film in different portions of the tube wall. A tube may have different number of fiber layers in different portions of the tube wall.

One or more laminates may be joined with adhesive. A polymer film may be placed on the outside, the inside or both sides of the balloon. A polymer may be sprayed brushed or coated onto the outside, the inside or both sides of the balloon. One or more laminates can be consolidated to form a tube. The consolidation process may allow the laminate layers to compact such that the ratio of fiber to adhesive in the tube walls after consolidation is greater than the ratio of fiber to adhesive in the tube walls before consolidation. The laminates can be combined to produce tubes with different mechanical properties.

A tube can have one or more laminates, adhesives, polymer films, or combinations thereof. The laminates, and/or adhesive, and/or polymer films can be consolidated into each other to form part or all of a tube. The flexible adhesive may remain flexible when cured or melted. The polymer films or films may melt or set during consolidation. The tube may be capable of sustaining pressure.

A very thin tube can be created via blow molding, rotational molding or some other technique. The tube may have a wall thickness of less than about 0.001 in. and be made of a low compliance polymer such as PET or Nylon. The tube may be a fiber reinforced tube. The tube may be inflated. Laminates may be laid on the surface of the tube. The laminates may have adhesive applied to them. The tube, together with some laminates, may be placed in a female mold with the tube still under pressure. The pressure in the tube can be further increased to provide increased force against the walls of the female mold. The laminates may be consolidated to form a tube. The tube may merge or bond with the laminates.

Method of Use

A tool 500 (which also can be referred to herein as a medical device) may be an endoscope, a laparoscope, a robotic surgical tool, a catheter or any other tool, instrument or device commonly inserted into the body as part of a medical procedure. The tool 500 may be flexible or rigid, or have portions which are flexible and portions which are rigid. The flexible parts of the tool 500, if present, may be actuated by a drive mechanism such that the device can form different shapes during a procedure. The actuation may be provided manually or by an electromagnetic actuator or by the use of air or fluid pressure. The one or more tools 500 can be non-robotic surgical tools, robotic surgical tools or combinations thereof. The tool 500 may be used as part of a natural orifice transluminal endoscopic surgery (NOTES) procedure.

The tool 500 can be part or all of a (e.g., the da Vinci Surgical System from Intuitive Surgical, Inc., Sunnyvale, Calif.; Sensei or Artisan from Hansen Medical, Inc., Mountain View, Calif.; or robotic or motorized colonoscopy devices from Olympus Corporation, Japan, Pentax/Hoya Corporation, Japan).

FIG. 36 shows a portion of an articulating section 458 of a medical device. The articulating section may be composed of one piece links 460 that are rotatably attached to each other such that they form a pivot 464. The pivot 464 may be formed by pressing two links, 460a and 460b, together. The pivot may be formed by passing a pin through both links. The medical device may have cables threaded thru holes 462. Pulling these cables in combination or alone can induce a controlled articulation of an articulating section 458 of a medical device.

FIG. 37 shows a portion of an articulating section 458 of a medical device, a distal end piece 466 and proximal end piece 468. Distal end piece 466 may include a camera, lighting, a surgical tool or tools, a balloon, or any other item commonly inserted into the body or combinations thereof. Proximal end piece 468 may connect the articulating section 458 to a larger medical instrument.

FIG. 38A shows a sheath 400 attached to a medical device 500.

FIGS. 38B, 38C and 38D shows a cross section of FIG. 38A. Articulating section 458 is shown enclosed within sheath 400. The radial clearance 473 between the sheath and the medical device may be from about 0 inches to about 0.25 inches, more narrowly from about 0 inches to about 0.05 inches, yet more narrowly from about 0 inches to about 0.015 inches.

Seal 420a has seal lip 470a which may be in contact with the medical device 500. Seal lip 470a may grasp medical device 500 firmly such that seal lip 470a may not readily slide or may have a fit such that it can readily slide. Seal 420b has a seal lip 470B which may be in contact with the medical device. Seal lip 470B may locate in groove 472 on medical device 500. Seal lip 470B and groove 472 may restrain seal 420b from longitudinal movement along the medical device 500. Groove 472 may be a groove, notch, stop or visible marking. Groove 472 may be used as a locating feature for seals 420a and 420b. Seals 470a and 470b may substantially longitudinally fix the sheath with respect to the medical device 500.

Seal lips 470a and 470b may prevent the passage of bodily fluids from outside the volume enclosed by the sheath 400 to inside the volume enclosed by the sheath. Seal lips 470a and 470b may allow the volume enclosed by the sheath 400 to be placed at a higher or lower pressure than the pressure found in the volume outside that enclosed by the sheath. Placing the volume enclosed by the sheath at a different pressure than the pressure surrounding the sheath and checking for leaks may allow a surgeon to check if sheath 400 is leak-tight.

FIG. 38E shows that the articulating section 458 of medical device 500 can easily flex while enclosed by sheath 400. At inside corner of the sheath bend 474, wrinkles may form on the sheath (not shown in the drawing).

FIGS. 39A and 39B show a sheath 400 covering a portion of an medical device 500. The medical device may be driven into a human body thru a cannula 476 by control system 474 towards target 478 within the body a patient. Control system 474 may be operated by a human, may be semi-autonomous or autonomous. Control system 474 may be robotic or non-robotic system. The robotic system can have actuation and a feedback loop to control position, velocity or acceleration of some portion of the medical device 500.

FIG. 39A shows the medical device in a first position approaching the target 478. FIG. 39B shows the medical device in a second position having reached target 478. The longitudinal sheath length 412 in the first position can be less than about 10% different (i.e., longer or short) than the longitudinal sheath length 412 in the second position. The longitudinal length of the medical device covered by the sheath can change by less than 10% (i.e., longer or shorter) between the first and second positions. The distal and/or proximal ends of the sheath can be fixed or move slightly (i.e., less than about 10% combined change in length, as stated above) or move significantly (i.e., more than about 10% combined change in length, as stated above) with respect to the tool 500. At the inside corner of the sheath bend 474, wrinkles may form on the sheath (not shown).

Figure 40B:
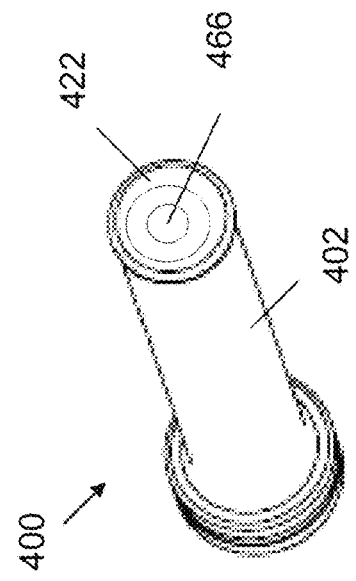
FIGS. 40A and 40B illustrate a variation of the device.
Figure 40A:
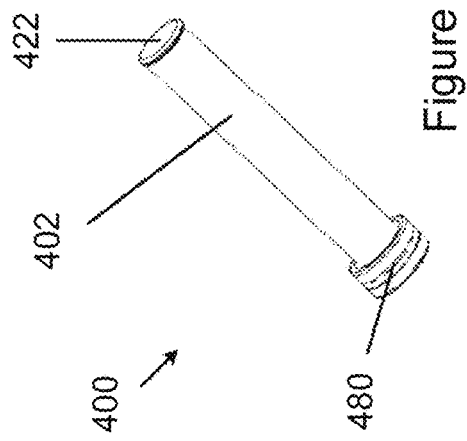
Figure 40C:
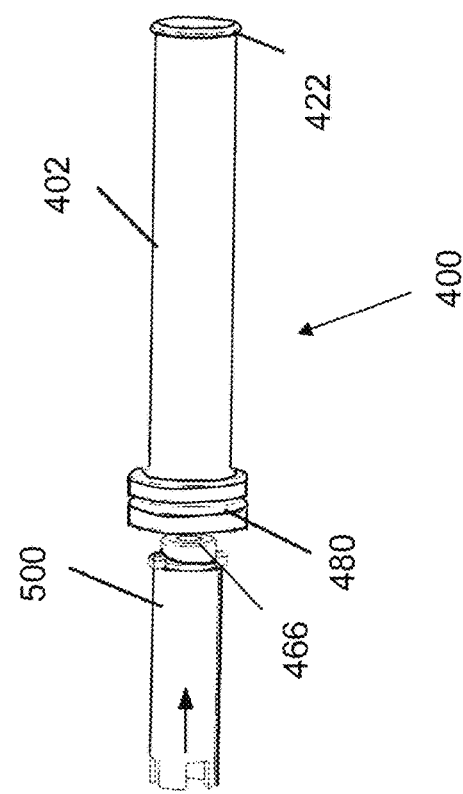
FIG. 40C illustrate a variation of a method for placing a variation of a device onto a medical device.

FIGS. 40A and 40B show a sheath 400 that could be placed over a medical device 500. Sheath 400 has tube 402, endcap 422 and collar 480 containing a seal. The distal end 466 of the medical device may be seen thru clear endcap 422 in FIG. 11B. Endcap 422 may be clear, may contain a lens or lenses, may have anti-reflection coatings, or may be designed to not obstruct certain wavelengths of light useful to a procedure. FIG. 40C shows a medical device 500 being inserted into sheath 400.

FIGS. 41A and 41B show a portion of sheath 400 placed over a portion of medical device 500. The flexible medical device 500 has end 466 that is not covered by the sheath but is substantially flush with the end of the sheath. FIG. 41A shows a portion of the flexible medical device in an approximately straight configuration. FIG. 41B shows a portion of the medical device in an approximately right angle configuration. At inside corner of the sheath bend 474, wrinkles may form on the sheath (not shown in the drawing). During the course of operation of the medical device, the sheath may get pinched or crimped by the motion of the medical device. For instance, the sheath may be caught between links 460 of the medical device. The design of the sheath may allow the sheath to resist puncture during pinching, crimping or catching derived from the medical device or by devices surrounding the outside of the sheath.

FIG. 42 shows a portion of sheath 400 placed over a portion of medical device 500. Medical device 500 has distal tip 466. Medical device 500 has an articulating section 458 near its tip 466. The distal end of sheath 400 is located proximal to articulating section 458.

Figure 43:
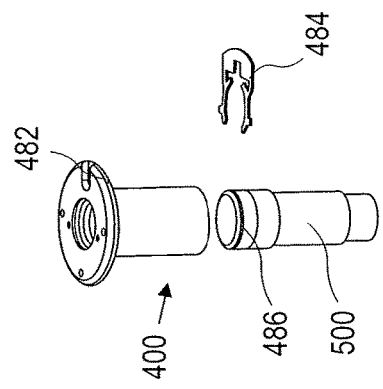

FIG. 43 shows medical device 500 with circular groove or other shear geometry 486 on the distal end of the medical device. A portion 400 of a sheath is shown. The portion 400 of the sheath has a fitting on the distal end with a slot 482. Clip 484 is shown before being inserted FIGS. 44A and 44B show the connection of medical device 500 and sheath portion 400. Clip 484 fits into both slot 482 and slot 486 to secure the medical device 500 to sheath portion 400. Boss 488 serves to reinforced clip 484.

Figure 44B:
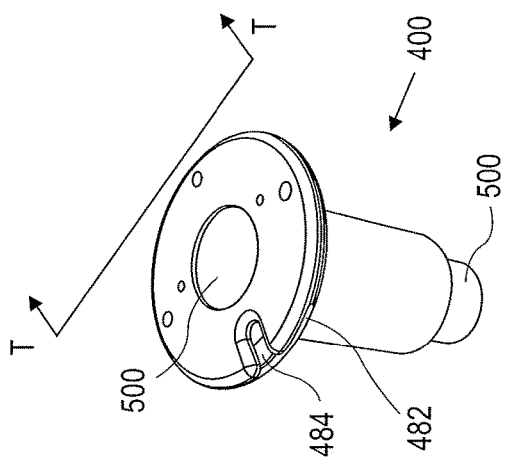
FIGS. 43, 44A and 44B illustrate a variation of a method for attaching the device to a medical device.
Figure 44A:
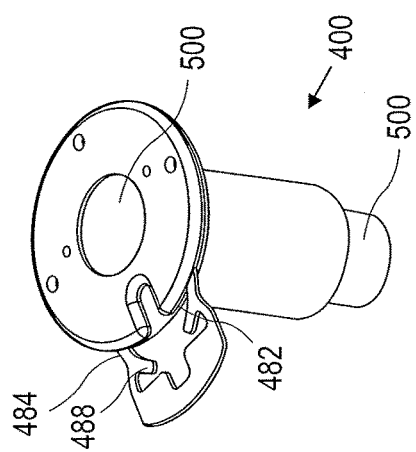
Figure 44C:
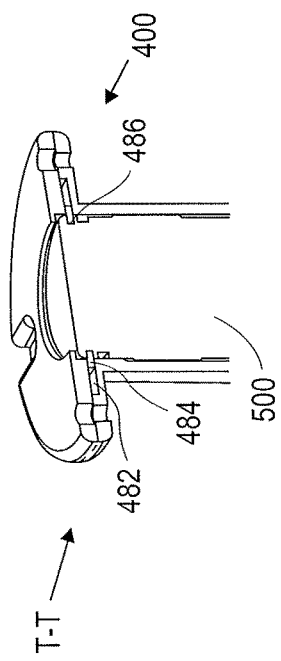
FIG. 44C illustrates a variation of a cross-section view T-T of FIG. 44B.

FIG. 44C shows a cross section of FIG. 44B.

Multiple sheaths may be used over one medical device: The sheaths could be placed at different points along the longitudinal axis of the medical device such that the sheaths do not overlap.

One sheath could be placed over a second sheath, both sheaths covering the medical device. One sheath could be disposed of after fewer procedures than the second sheath.

The sheath may be permanently attached to the medical device. The sheath may only extend over sections of the medical device that can be articulated.

Sheath 400 may be affixed to a medical device during the manufacture of the medical device. Sheath 400 may be affixed to the medical device by a medical professional before use in a procedure. A sheath may be used during a single procedure and then disposed of. A sheath may be used for t or more procedures and then disposed of A sheath may be a permanent part of a medical device. A sheath may be cleaned after each procedure.

The sheath may need to resist puncture during the medical procedure employing the medical device. The sheath may be punctured by structures in the body, such as bone. The sheath may be punctured by the motion of the medical device against the sheath. The medical device may be a flexible structure. The medical device may contain discrete joints that can pinch the sheath.

Tubes may need to be packed to the smallest possible size when entering and exiting the body. Pleating or fluting the tube walls is typical. Pleating may be accomplished by placing the tube into a mechanical fixture and then heating the tube to approximately 80° C. for 1 minute. The heat will cause the tube to reflect the geometry of the mechanical fixture.

The sheath may need to resist puncture while exposed to extreme cold during, for instance, a medical procedure involving a cryogenic liquid.

A sheath may include a tube. A sheath can be a sleeve, a drape, a covering, a blood barrier or a biological barrier.

The sheath may need to be made and sold for a low cost.

The sheath may need to be flexible enough to not significantly interfere with the function of the medical device.

It will be appreciated by those skilled in the art having the benefit of this disclosure that this invention provides a fiber reinforced sheath. It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, combinations, substitutions, alternatives, design choices, and embodiments apparent to those of ordinary skill in the art, without departing from the spirit and scope of this invention.

We claim:

1. A method for using a tool in or on a patient's body, comprising:
    attaching a distal end of a fiber-reinforced first sheath to a tool at a fixed longitudinal position with respect to the tool, wherein the tool is radially within the fiber-reinforced first sheath;
    sealing the first sheath to the tool, wherein the sealing step includes sealing a proximal end of the sheath to a portion of the tool by placing a proximal seal lip located at the proximal end of the sheath in contact with the portion of the tool, said portion of the tool comprising an outer surface substantially parallel to a longitudinal axis of the tool such that the proximal seal lip is adapted to slide along the outer surface of the portion of the tool; and
    deploying the tool to a target site in or on a patient's body for therapy or diagnostic use, wherein deploying includes moving the tool between a first position and a second position, wherein the fiber-reinforced first sheath bends from a first point when the tool is in the first position to a second point when the tool is in the second position, wherein the fiber-reinforced first sheath has a tensile strength of greater than about 138 MPa.

2. The method of claim 1, wherein the first sheath further comprises a laminate and a reinforcement member, wherein the reinforcement member is more rigid than the laminate, and wherein the reinforcement member is substantially helical.

3. The method of claim 1, wherein deploying comprises controlling a robotic system to move the tool.

4. The method of claim 1, wherein the sealing step further includes sealing the distal end of the first sheath to the tool.

5. The method of claim 1, wherein the sealing step further includes providing a cap to the distal end of the sheath.

6. The method of claim 1, wherein the attaching step further comprises preventing the first sheath from any longitudinal movement along the tool.

7. The method of claim 1, wherein the attaching step further comprises clipping the first sheath to the tool.

8. The method of claim 1, wherein the attaching step further comprises positioning the first sheath partially over the tool.

9. The method of claim 1, wherein the attaching step comprises placing an internally extending radial extension associated with the first sheath in contact with the tool.

10. The method of claim 9, wherein the internally extending radial extension is on a distal end of the first sheath and the attaching step further comprises placing the internally extending radial extension in contact with one of a groove, notch, stop or visible marking associated with the tool.

11. The method of claim 1, wherein the deploying step comprises bending the tool from the first position to the second position.

12. The method of claim 1, wherein the tool includes a plurality of articulating sections including at least one pivot point therebetween along a longitudinal axis of the tool, and wherein the step of moving the tool between the first position and the second position comprises bending the tool at the pivot point, said pivot point located between the proximal end of the first sheath and the distal end of the first sheath.

13. A method for using a tool in or on a patient's body comprising:
    sealing a distal end of a fiber-reinforced first sheath to the tool, said distal end of the first sheath including a lip for engaging the tool, wherein the tool is radially within the fiber-reinforced first sheath, and wherein the sealing comprises sealing the lip to the tool at a fixed longitudinal position with respect to the tool;
    sealing a proximal end of the first sheath to a portion of the tool by placing a proximal seal lip located at the proximal end of the first sheath in contact with the portion of the tool, said portion of the tool comprising an outer surface substantially parallel to a longitudinal axis of the tool such that the proximal seal lip is adapted to slide along the outer surface of the portion of the tool; and
    deploying the tool to a target site in or on the patient's body for therapy or diagnostic use, wherein deploying includes bending the tool and the first sheath sealed to the tool between a first position and a second position, wherein the fiber-reinforced first sheath has a tensile strength of greater than about 138 MPa.

14. The method of claim 13, wherein the step of sealing the distal end of the first sheath to the tool includes sealing the lip of the first sheath to means for engaging the lip, said means for engaging being associated with the tool.

15. The method of claim 13, wherein the sealing of the distal end of the sheath to the tool and the sealing of the proximal end of the sheath to the tool are adapted to allow less than about 10% change in length of the sheath in moving the tool between the first position and the second position.

16. The method of claim 13, wherein the sealing of the distal end of the sheath to the tool and the sealing of the proximal end of the sheath to the tool are adapted to allow greater than about 10% change in length of the sheath in moving the tool between the first position and the second position.

* * * * *